(12) United States Patent
Paul et al.

(10) Patent No.: US 7,276,064 B2
(45) Date of Patent: Oct. 2, 2007

(54) SIDE-PORT SHEATH FOR CATHETER PLACEMENT AND TRANSLATION

(75) Inventors: Saurav Paul, Minneapolis, MN (US); Kedar Ravindra Belhe, Minnetonka, MN (US); Hong Cao, Shakopee, MN (US); John Avi Roop, Crystal, MN (US); Chou Thao, Brooklyn Park, MN (US)

(73) Assignee: St. Jude Medical, Atrial Fibrillation Division, Inc., Maple Grove, MN (US)

( * ) Notice: Subject to any disclaimer, the term of this patent is extended or adjusted under 35 U.S.C. 154(b) by 180 days.

(21) Appl. No.: 10/856,145

(22) Filed: May 27, 2004

(65) Prior Publication Data

US 2005/0267458 A1   Dec. 1, 2005

(51) Int. Cl.
 *A61B 18/14* (2006.01)
(52) U.S. Cl. .................................. 606/41; 607/122
(58) Field of Classification Search ............. 606/41
See application file for complete search history.

(56) References Cited

U.S. PATENT DOCUMENTS

| | | | |
|---|---|---|---|
| 4,552,554 A * | 11/1985 | Gould et al. | 604/506 |
| 4,565,200 A * | 1/1986 | Cosman | 600/373 |
| 4,774,949 A * | 10/1988 | Fogarty | 606/108 |
| 4,905,667 A * | 3/1990 | Foerster et al. | 600/104 |
| 4,950,267 A * | 8/1990 | Ishihara et al. | 606/12 |
| 4,961,047 A * | 10/1990 | Carder | 323/322 |
| 5,041,109 A * | 8/1991 | Abela | 606/15 |
| 5,354,279 A * | 10/1994 | Hofling | 604/164.12 |
| 5,366,490 A * | 11/1994 | Edwards et al. | 607/99 |
| 5,423,808 A * | 6/1995 | Edwards et al. | 606/34 |
| 5,487,385 A * | 1/1996 | Avitall | 600/374 |
| 5,687,723 A | 11/1997 | Avitall | |
| 5,785,706 A | 7/1998 | Bednarek | |
| 5,842,984 A | 12/1998 | Avitall | |
| 5,891,133 A * | 4/1999 | Murphy-Chutorian | 606/7 |
| 5,921,924 A | 7/1999 | Avitall | |
| 5,944,715 A * | 8/1999 | Goble et al. | 606/41 |
| 6,013,076 A * | 1/2000 | Goble et al. | 606/41 |
| 6,015,406 A * | 1/2000 | Goble et al. | 606/41 |
| 6,042,581 A * | 3/2000 | Ryan et al. | 606/45 |
| 6,044,846 A * | 4/2000 | Edwards | 128/898 |
| 6,068,629 A | 5/2000 | Haissaguerre et al. | |
| 6,071,274 A | 6/2000 | Thompson et al. | |
| 6,071,279 A | 6/2000 | Whayne et al. | |
| 6,076,012 A | 6/2000 | Swanson et al. | |
| 6,129,726 A * | 10/2000 | Edwards et al. | 606/41 |
| 6,138,043 A | 10/2000 | Avitall | |
| 6,190,353 B1 * | 2/2001 | Makower et al. | 604/95.01 |

(Continued)

FOREIGN PATENT DOCUMENTS

WO    WO95/10319    4/1995

*Primary Examiner*—Michael Peffley
*Assistant Examiner*—Alex Toy
(74) *Attorney, Agent, or Firm*—Heimbecher & Assoc., LLC

(57) ABSTRACT

Side-port sheaths for catheter placement and translation are disclosed. The sheaths include a side-port opening through which a gliding catheter may be deployed during diagnosis or treatment of tissue. The side-port sheath may include a suspension ribbon used to deploy, or that aids in the deployment of, the embedded gliding catheter. The suspension ribbon may be slideably or fixably engaged with an outer surface of the sheath of the gliding catheter.

17 Claims, 22 Drawing Sheets

U.S. PATENT DOCUMENTS

| | | |
|---|---|---|
| 6,217,527 B1 * | 4/2001 | Selmon et al. ............... 600/585 |
| 6,235,021 B1 * | 5/2001 | Sieben ........................ 606/41 |
| 6,241,754 B1 | 6/2001 | Swanson et al. |
| 6,264,650 B1 * | 7/2001 | Hovda et al. ................. 606/32 |
| 6,283,951 B1 * | 9/2001 | Flaherty et al. ............. 604/529 |
| 6,302,875 B1 * | 10/2001 | Makower et al. ........... 604/528 |
| 6,308,091 B1 | 10/2001 | Avitall |
| 6,314,962 B1 | 11/2001 | Vaska et al. |
| 6,314,963 B1 | 11/2001 | Vaska et al. |
| 6,330,473 B1 | 12/2001 | Swanson et al. |
| 6,379,319 B1 * | 4/2002 | Garibotto et al. ........... 600/585 |
| 6,454,758 B1 | 9/2002 | Thompson et al. |
| 7,004,173 B2 * | 2/2006 | Sparks et al. ............... 128/898 |
| 2003/0208195 A1 | 11/2003 | Thompson et al. |

\* cited by examiner

SIDE-PORT SHEATH FOR CATHETER PLACEMENT AND TRANSLATION

BACKGROUND OF THE INVENTION a. Field of the Invention

The instant invention is directed toward a device and method for the placement and translation of a catheter in a body cavity. More specifically, it relates to a side-port sheath through which a catheter for diagnosis or treatment of tissue may be placed adjacent to, or in contact with, tissue to be diagnosed or treated.

b. Background Art

It is well known that benefits may be gained by forming lesions in tissue if the depth and location of the lesions being formed can be controlled. In particular, it can be desirable to elevate tissue temperature to around 50° C. until lesions are formed via coagulation necrosis, which changes the electrical properties of the tissue. For example, when sufficiently deep lesions are formed at specific locations in cardiac tissue via coagulation necrosis, undesirable atrial fibrillations may be lessened or eliminated. "Sufficiently deep" lesions means transmural lesions in some cardiac applications.

Several difficulties may be encountered, however, when attempting to form adequately-deep lesions at specific locations using some existing ablation catheters and electrodes. For example, when forming lesions with RF energy, high temperature gradients are often encountered in the vicinity of the electrode. At the edges of some existing electrodes are regions of very high current density, leading to large temperature gradients and hot spots. These "edge effects" may result in the formation of undesirable coagulum and charring of the surface tissue. For example, undesirable coagulum may begin to form when blood reaches around 80° C. for an appreciable length of time, and undesirable tissue charring and desiccation may be seen when tissue reaches around 100° C. for an appreciable length of time. There two types of undesirable coagulum: coagulum that adheres to and damages the medical device (e.g., the electrode); and coagulum blood clots or curds that may enter a patient's bloodstream, possibly resulting in other health problems for the patient. Charring of the surface tissue may also have deleterious effects on a patient.

As the temperature of the electrode is increased, the contact time required to form an adequately-deep lesion decreases, but the likelihood of charring surface tissue and forming undesirable coagulum increases. As the temperature of the electrode is decreased, the contact time required to form an adequately-deep lesion increases, but the likelihood of charring surface tissue and forming undesirable coagulum decreases. It is, therefore, a balancing act trying to ensure that tissue temperatures are adequately high for long enough to create deep lesions, while still preventing or minimizing coagulum formation and/or charring of the surface tissue. Active temperature control may help, but the placement of thermocouples, for example, is tricky and setting the RF generator for a certain temperature becomes an empirical exercise as actual tissue temperatures are generally different from those recorded next to the electrode due to factors such as convection and catheter design.

Another difficulty encountered with existing ablation electrodes is how to ensure adequate tissue contact. Current techniques for creating continuous linear lesions in endocardial applications include, for example, dragging a conventional catheter on the tissue, using an array electrode, or using pre-formed electrodes. All of these devices comprise rigid electrodes that do not always conform to the tissue surface, especially when sharp gradients and undulations are present, such as at the ostium of the pulmonary vein in the left atrium and the isthmus of the right atrium. Consequently, continuous linear lesions are difficult to achieve. When forming lesions in a heart, the beating of the heart further complicates matters, making it difficult to keep adequate contact between the electrode and the tissue for a sufficient length of time to form a desired lesion. With a rigid electrode, it can be quite difficult to maintain sufficient contact pressure until an adequate lesion has been formed. This problem is exacerbated on contoured or trabeculated surfaces. If the contact between the electrode and the tissue cannot be properly maintained, a quality lesion is unlikely to be formed.

Catheters based upon a virtual electrode may address some of the difficulties, but these catheters often require high flow rates of conductive fluid (e.g., typically around 70 milliliters per minute) to maintain effective cooling for high-power RF applications. The introduction of a large amount of conductive fluid (used to flush-cool the catheter electrode) into a patient's bloodstream may have detrimental effects on the patient.

Uncontrolled electric field leakage from the circumference of an electrode (e.g., from the outer surface of the electrode) can also be a problem. In particular, many existing devices permit the ablative energy to "leak" from the electrode away from the tissue to be ablated rather than being focused toward the tissue. This electric field leakage may reduce the efficacy of an ablation device.

Thus, there remains a need for an ablation catheter that address these issues with the existing designs and that permits the formation of uniform, transmural spot and continuous linear lesions on smooth or contoured surfaces.

BRIEF SUMMARY OF THE INVENTION

It is desirable to be able to treat tissue by forming adequately-deep spot or continuous linear lesions in the tissue while reducing the formation of undesirable coagulum and charring of the surface tissue, while applying a reasonable amount of RF energy, while mitigating electrode-tissue contact problems, and/or while reducing the amount of conductive fluid (e.g., isotonic saline) possibly entering a patient's bloodstream during the procedure. It is also desirable to be able to diagnose tissue using electrical or chemical feedback from the tissue. The side-port sheath of the present invention facilitates improved diagnosis or treatment of tissue.

In one form, the present invention comprises a side-port sheath having a tip, wherein the tip further has a sidewall; a side-port opening that extends through the sidewall from a proximal opening edge to a distal opening edge; and an internal, gliding surface that extends from a leading edge to a trailing edge, wherein the trailing edge of the gliding surface is adjacent to the distal edge of the side-port opening.

In another form the present invention comprises a side-port sheath that has a tip, a shaft, and a suspension ribbon. The tip further comprises a proximal end and a distal end, wherein the distal end comprises a blunt nose; a first tip sidewall, wherein a ribbon containment cavity is formed in the first tip sidewall; a second tip sidewall that is radially offset from the first tip sidewall by 180 degrees; a tip side-port opening that extends through the second tip sidewall from a side-port opening proximal edge to a side-port opening distal edge; and an internal, gliding surface that extends from a leading edge to a trailing edge, wherein the trailing edge of the gliding surface is adjacent to the side-port opening distal edge. The shaft further comprises a distal end that meets the proximal end of the tip; a first shaft sidewall, wherein a ribbon channel extends longitudinally within the first shaft sidewall; and a second shaft sidewall that is radially offset from the first shaft sidewall by 180 degrees. The suspension ribbon comprises a distal end and is adapted to form a bowed leaf spring. The suspension ribbon is slideably mounted in the ribbon channel, and the distal end of the suspension ribbon is supported by the ribbon containment cavity.

In yet another form, the present invention comprises a device for the diagnosis or treatment of tissue in a body cavity, the device comprising a side-port sheath and an electrophysiology catheter. The side-port sheath comprises a tip, wherein the tip further comprises a tip sidewall; a tip side-port opening that extends through the tip sidewall from a proximal opening edge to a distal opening edge; and an internal, gliding surface that extends from a leading edge to a trailing edge, wherein the trailing edge of the gliding surface is adjacent to the distal edge of the side-port opening.

In still another form, the present invention comprises a device for the diagnosis or treatment of tissue in a body cavity, the device again comprising a side-port sheath and an electrophysiology catheter. The side-port sheath comprises a tip, a shaft, and a suspension ribbon. The tip further comprises a proximal end and a distal end, wherein the distal end comprises a blunt nose; a first tip sidewall, wherein a ribbon containment cavity is formed in the first tip sidewall; a second tip sidewall that is radially offset from the first tip sidewall by 180 degrees; a tip side-port opening that extends through the second tip sidewall from a side-port opening proximal edge to a side-port opening distal edge; and an internal, gliding surface that extends from a leading edge to a trailing edge, wherein the trailing edge of the gliding surface is adjacent to the distal edge of the tip side-port opening. The shaft further comprises a distal end that matches up with the proximal end of the tip; a first shaft sidewall, wherein a ribbon channel extends longitudinally within the first shaft sidewall; and a second shaft sidewall that is radially offset from the first shaft sidewall by 180 degrees. The suspension ribbon further comprises a distal end. The suspension ribbon is slideably mounted in the ribbon channel, and the distal end of the suspension ribbon is supported by the ribbon containment cavity. The suspension ribbon is adapted to form a bowed leaf spring. The device may further comprises a ribbon guide that links the suspension ribbon to the electrophysiology catheter.

The present invention also comprises a method of placing and translating a catheter in a body cavity having tissue to be diagnosed or treated. In particular, the method comprises the step of assembling a side-port sheath comprising a tip, wherein the tip further comprises a tip sidewall; a tip side-port opening that extends through the tip sidewall from a proximal edge to a distal edge; and an internal, gliding surface that extends from a leading edge to a trailing edge, wherein the trailing edge of the gliding surface is adjacent to the distal edge of the tip side-port opening. The method further comprises the steps of inserting an electrophysiology catheter having a working portion into the side-port sheath, with the working portion fully housed within the tip of the side-port sheath and adjacent to the tip side-port opening; positioning the side-port sheath into a body cavity with the tip side-port opening adjacent to the tissue to be diagnosed or treated; and deploying and retracting the electrophysiology catheter by pushing the electrophysiology catheter toward the gliding surface of the side-port sheath until the working portion of the electrophysiology catheter at least partially exits the tip side-port opening and pulling the electrophysiology catheter back into the side-port sheath. The configuration of the gliding surface may be adjusted for a particular application. In addition to, or as an alternative to, moving the electrophysiology catheter within the side-port sheath, the side-port sheath itself may be translated.

In yet another form, the present invention comprises a method of placing and translating a catheter in a body cavity having tissue to be diagnosed or treated, the method comprising the steps of assembling a side-port sheath; inserting an electrophysiology catheter having a working portion into the side-port sheath; positioning the side-port sheath into a body cavity having tissue to be diagnosed or treated; and pushing the electrophysiology catheter toward the tissue. The assembling step includes assembling a side-port sheath comprising a tip, a shaft, and a suspension ribbon. The tip comprises a proximal end and a distal end, wherein the distal end comprises a blunt nose; a first tip sidewall, wherein a ribbon containment cavity is formed in the first tip sidewall; a second tip sidewall that is radially offset from the first tip sidewall by 180 degrees; a tip side-port opening that extends through the second tip sidewall from a side-port opening proximal edge to a side-port opening distal edge; and an internal, gliding surface that extends from a leading edge to a trailing edge, wherein the trailing edge of the gliding surface is adjacent to the distal edge of the tip side-port opening. The shaft comprises a distal end that is connected with the proximal end of the tip; a first shaft sidewall, wherein a ribbon channel extends longitudinally within the first shaft sidewall; and a second shaft sidewall that is radially offset from the first shaft sidewall by 180 degrees. The suspension ribbon is slideably mounted in the ribbon channel, and the suspension ribbon further comprises a distal end that is supported by the ribbon containment cavity. The inserting step further comprises inserting an electrophysiology catheter having a working portion into the side-port sheath with the working portion initially fully housed with the side-port sheath and adjacent to the tip side-port opening. The positioning step further comprises positioning the side-port sheath into a body cavity having tissue to be diagnosed or treated. The pushing step further comprises pushing the suspension ribbon toward the ribbon containment cavity, thereby forming a bowed leaf spring from a portion of the suspension ribbon that pushes the electrophysiology catheter toward the tip side-port opening.

The foregoing and other aspects, features, details, utilities, and advantages of the present invention will be apparent from reading the following description and claims, and from reviewing the accompanying drawings.

DETAILED DESCRIPTION OF THE INVENTION

A number of embodiments of a diagnostic or treatment device (e.g., 10 in FIG. 1) comprising a side-port sheath (e.g., 12 in FIG. 1) according to the present invention are depicted in the figures. The side-port sheath facilitates placement and translation of a diagnostic or treatment catheter (e.g., 14 in FIG. 1) adjacent to, or in contact with, tissue to be diagnosed or treated. The catheter may, for example, include an electrode (e.g., 16 in FIG. 1) for delivering ablative energy to tissue, or the catheter may receive electrical or chemical information from the tissue.

As described further below, the side-port sheath of the present invention provides a number of advantages, including, for example, the ability to enhance ablation efficiency by (a) controlling electric field leakage from the circumference of a catheter electrode (e.g., the outer surface of a brush electrode) and allowing the electric field to pass only through a side-port opening (e.g., 18 in FIG. 1) and into the tissue; (b) preventing ambient fluid (e.g., blood) from coming into contact with the catheter electrode, thereby mitigating coagulum formation on the electrode; and (c) preventing the ambient fluid from mixing with infused fluid (e.g., saline), when present, used to flush-cool the catheter electrode (e.g., conductive or nonconductive fluid that may be used with the brush electrode depicted in several of the drawings). In some embodiments of the present invention, additional features are present to enhance tissue contact in difficult environments (e.g., during ablation of a contoured or trabeculated tissue surface inside a beating heart), whether creating a spot lesion or a continuous linear lesion.

Figure 1:
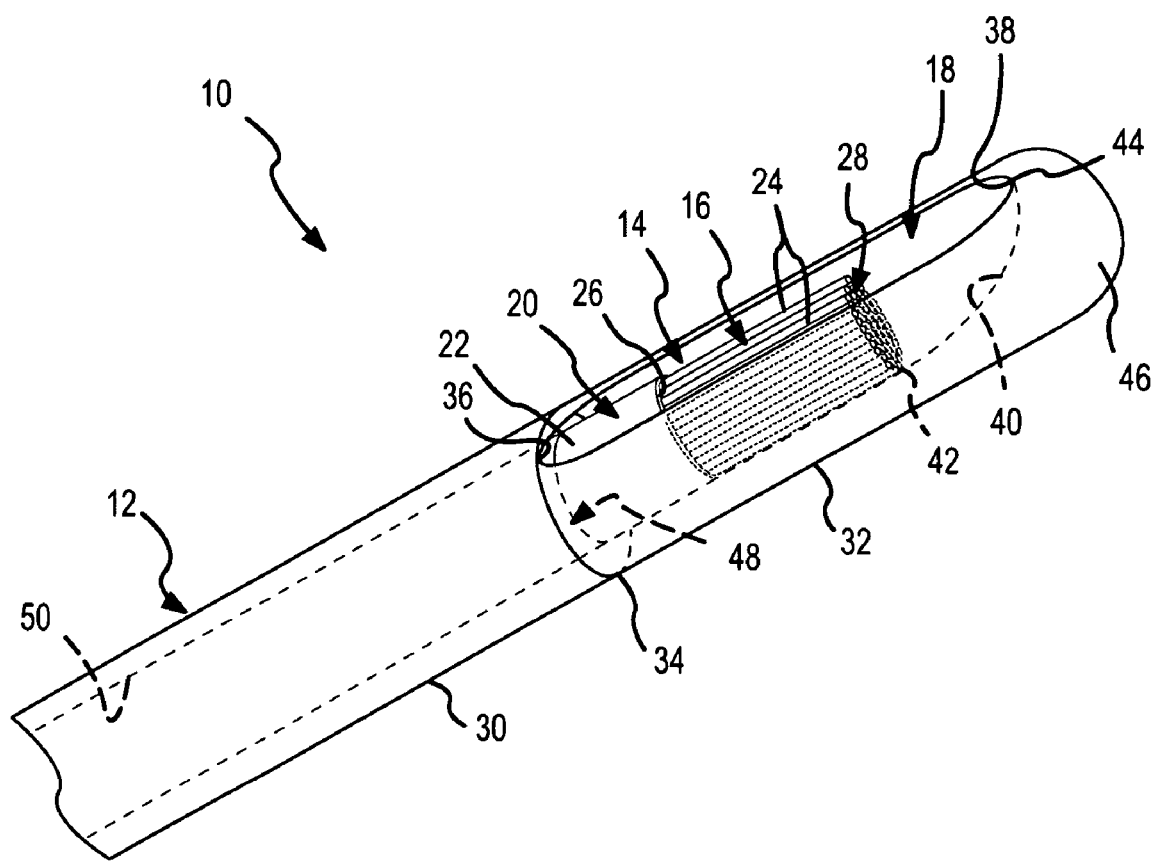
FIG. 1 is a fragmentary, isometric view of a diagnostic or treatment device comprising a side-port sheath according to a first embodiment of the present invention, and depicts an undeployed gliding catheter adjacent to an elongated side-port opening.

FIG. 1 is a fragmentary, isometric view of a diagnostic or treatment device 10 comprising a side-port sheath 12 according to a first embodiment of the present invention. The side-port sheath 12 is a main or outside catheter that facilitates placement and translation of a gliding or inside catheter 14. As alluded to above, the gliding catheter 14 may be any type of diagnostic or treatment catheter, such as an electrophysiology catheter or an ablation catheter (e.g., a wet-brush or a Livewire™ catheter available from St. Jude Medical). In FIGS. 1-27, the gliding catheter 14 is depicted as a brush electrode catheter, but, as explained further below in connection with FIGS. 28-32, a variety of different types of gliding catheters could be used with the side-port sheath of the present invention. As a brush electrode catheter, the gliding catheter 14 depicted in FIG. 1 comprises a catheter sheath 20 having an outside surface 22. A brush electrode 16 comprising a plurality of conductive and/or nonconductive filaments 24 extends from a distal edge 26 of the catheter sheath 20 to a working surface 28 of the brush electrode 16.

The side-port sheath 12 itself comprises a shaft 30 and a tip or ported nose 32, either or both of which may be porous. In FIG. 1, the shaft 30 and tip 32 are shown as separate components that are united at a seam 34, but the shaft and tip may comprise a single, unitary component. The tip 32 comprises an elongated, side-port opening 18 through a sidewall of the tip. This side-port opening 18 thus extends longitudinally along a section of the outer surface of the tip 32 from a proximal side-port opening edge 36 to a distal side-port opening edge 38. An internal, wedge-shaped gliding surface or curvilinear electrode ramp 40, may be seen in phantom in FIG. 1. This gliding surface includes a proximal or leading edge and a distal or trailing edge 44 that meets the distal edge 38 of the side-port opening 18. The blunt nose 46 of the tip 32 facilitates insertion of the diagnostic or treatment device 10 into position within, for example, a human heart (see, e.g., FIGS. 21-23) or other body cavity (see also FIGS. 3 and 27). The shaft 30 of the side-port sheath 12 has a longitudinally-extending lumen 48 that accommodates the catheter sheath. In particular, the lumen 48 of the side-port sheath 12 includes an inner surface 50 against which the outer surface 22 of the catheter sheath 20 slides in the embodiment depicted in FIG. 1.

As depicted in FIG. 1, the gliding catheter 14 is undeployed (i.e., the brush electrode 16 is fully housed within the tip 32 of the side-port sheath 12), but the brush electrode is positioned adjacent to the elongated side-port opening 18. As will be explained further below in connection with FIGS. 25 and 27, even an "undeployed" gliding catheter may be used, for example, to form a lesion. "Undeployed" thus merely defines the position of the gliding catheter electrode 16 relative to the side-port opening 18.

Figure 2:
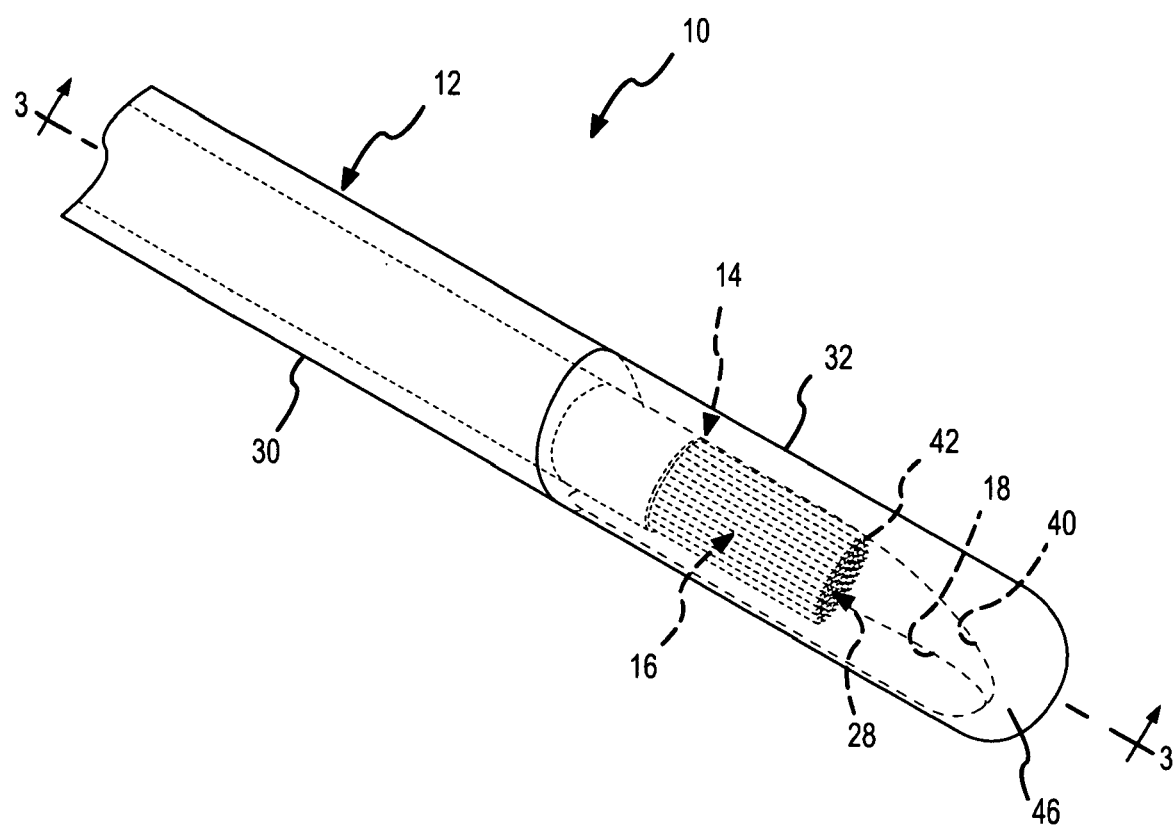
FIG. 2 is a fragmentary, isometric view of the diagnostic or treatment device depicted in FIG. 1 from a different angle, with the undeployed gliding catheter and the elongated, side-port opening shown completely in phantom.

FIG. 2 is a fragmentary, isometric view of the diagnostic or treatment device 10 depicted in FIG. 1 from a different angle. In this figure, the gliding catheter 14 and the gliding surface 40 are shown in phantom. The gliding catheter 14 is depicted in the same position relative to the side-port opening 18 that is shown in FIG. 1, with the working surface 28 of the brush electrode 16 just starting to engage the leading edge 42 of the gliding surface 40, and the brush electrode 16 of the gliding catheter 14 still fully enclosed within the tip 32 of the side-port sheath 12.

Figure 3:
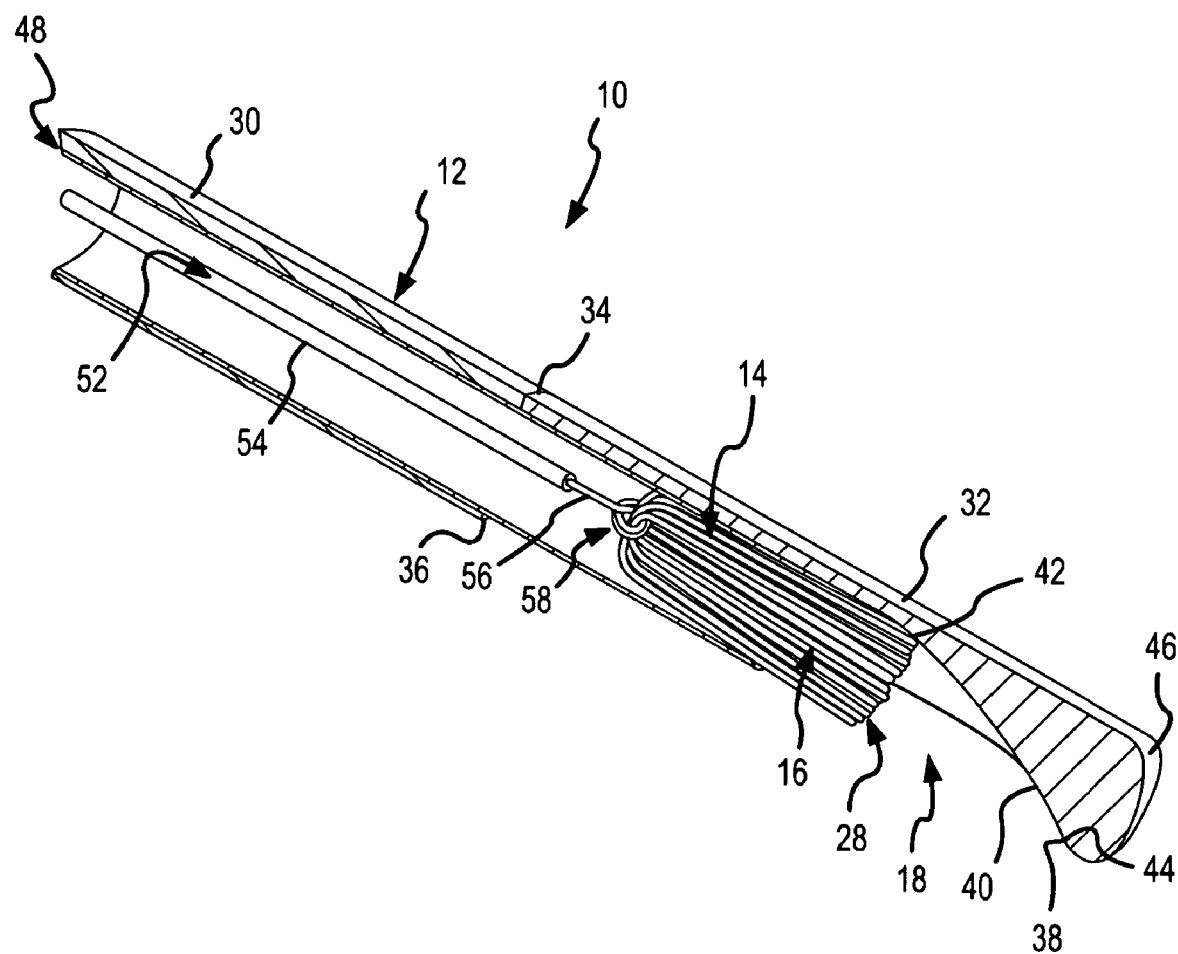
FIG. 3 is a fragmentary, isometric, cross-sectional view of the diagnostic or treatment device depicted in FIGS. 1 and 2 taken along line 3-3 of FIG. 2, with the gliding catheter depicted prior to being advanced into an internal, wedge-shaped gliding surface leading to a distal edge of the side-port opening.

FIG. 3 is a fragmentary, isometric, cross-sectional view of the diagnostic or treatment device 10 depicted in FIGS. 1 and 2 taken along line 3-3 of FIG. 2. Again, the electrode 16 of the gliding catheter 14 is depicted prior to being advanced against the internal, wedge-shaped gliding surface 40 that extends to the distal edge 38 of the side-port opening 18. Further details of the brush electrode catheter 14 may be seen in this figure. In particular, the conductor 52 of ablative energy is depicted as including an insulated portion 54 and an exposed portion 56. The exposed portion 56 is looped around the midpoint of the bundle of filaments 24 comprising the brush electrode 16 at a connection point 58. Again, a brush electrode catheter is depicted in the figures for illustrative purposes only, and a variety of different types of gliding catheters may be used with the side-port sheath of the present invention. As also shown in FIG. 3, the shaft 30 is separate from the tip 32, and the shaft and tip are joined at the seam 34. As previously mentioned, the shaft and tip may comprise a single, unitary piece. The working surface 28 at the distal end of the brush electrode 16 has been advanced just past, or distal of, the leading edge 42 of the gliding surface 40 and, thus, the electrode 16 of the gliding catheter 14 has just started being advanced towards the side-port opening 18.

Figure 4:
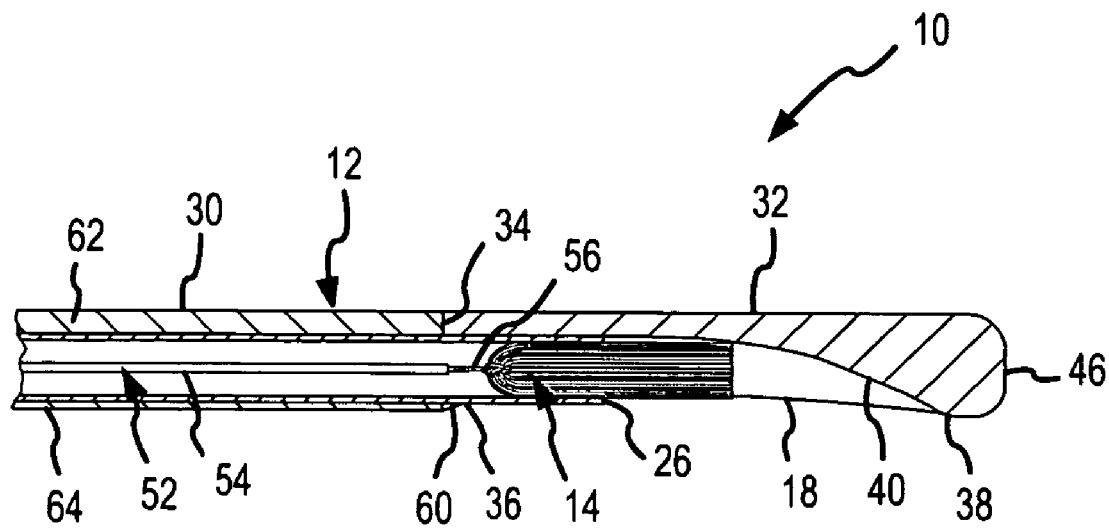
FIG. 4 is a fragmentary, cross-sectional view of the side-port sheath and gliding catheter of FIGS. 1-3 in the configuration that is also depicted in FIGS. 1-3.

FIG. 4 is a fragmentary, cross-sectional view of the side-port sheath 12 and gliding catheter 14 of FIGS. 1-3. As shown in this figure, a taper 60 may be present at the proximal edge 36 of the side-port opening 18 to facilitate insertion of the diagnostic or treatment device 10 into a body cavity. As also clearly shown in FIG. 4, the upper wall 62 (i.e., the wall on the opposite side of the diagnostic or treatment device from the side-port opening) may be thicker than the lower wall 64 for reasons explained further below.

Figure 5:
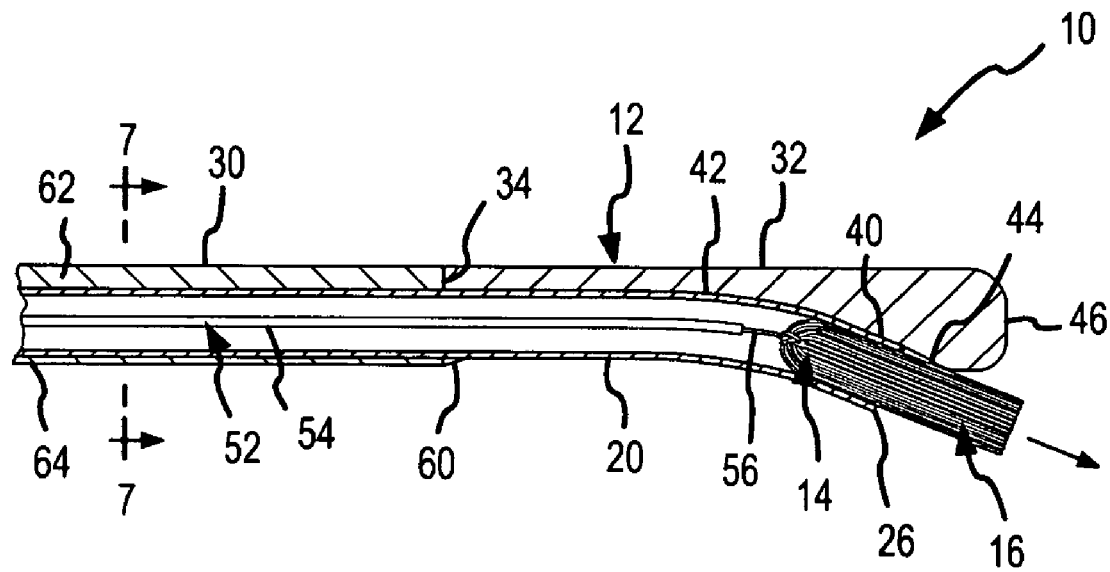
FIG. 5 is similar to FIG. 4, but depicts the gliding catheter in a deployed configuration after being guided against the wedge-shaped gliding surface and partially through the elongated, side-port opening.
Figure 6:
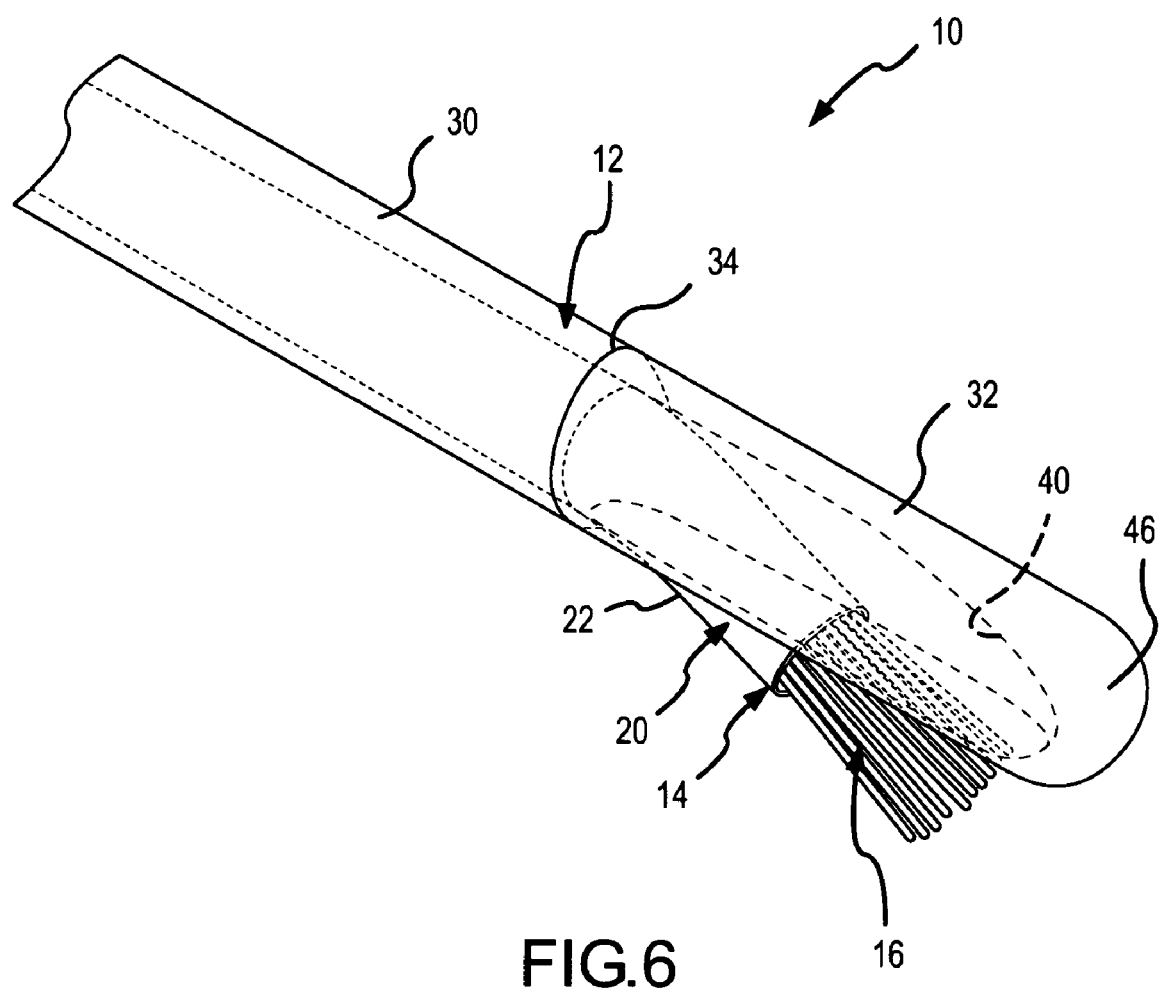
FIG. 6 is a fragmentary, isometric view of the diagnostic or treatment device of FIGS. 1-5 with the gliding catheter in the deployed configuration that is also depicted in FIG. 5.
Figure 8:
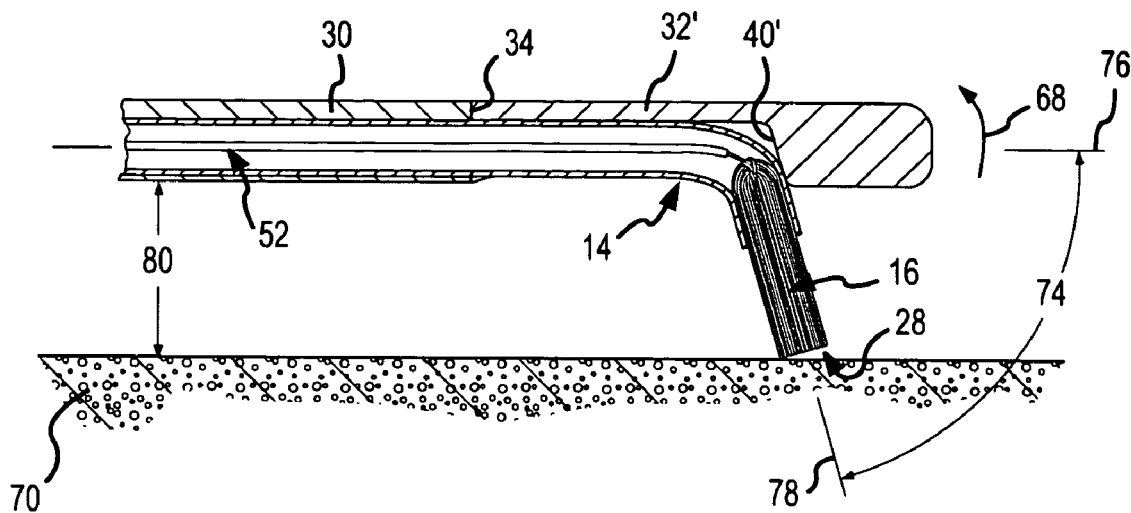
FIG. 8 is similar to FIG. 5, but depicts the gliding catheter being deployed toward tissue under the influence of a gliding surface that is more steeply sloped than the gliding surface depicted in FIG. 5.
Figure 9:
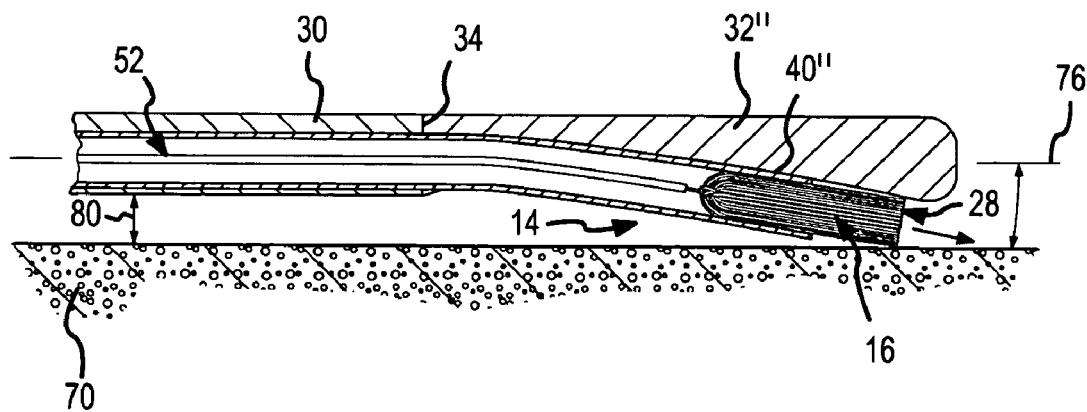
FIG. 9 is similar to FIGS. 5 and 8, but depicts the gliding catheter being deployed toward tissue under the influence of a gliding surface that is less steeply sloped than the gliding surfaces depicted in FIGS. 5 and 8.

FIG. 5 is similar to FIG. 4, but depicts the gliding catheter 14 in a deployed configuration. In particular, in FIG. 5, a portion of the electrode 16 extends through the side-port opening 18 and away from the outer surface of the tip 32 of the side-port sheath 12. In this configuration, the gliding catheter 14 has been advanced distally, and the distal edge 26 of the catheter sheath 20 has advanced part way between the leading edge 42 of the gliding surface and the trailing edge 44 of the gliding surface 40. The diagnostic or treatment device 10 improves catheter-tissue contact by allowing catheter placement at variable incidence angles of contact (see, e.g., 74 in FIG. 8) in trabeculated regions of, for example, the myocardium. Thus, as shown in FIGS. 8 and 9, and as explained further below, the electrode incidence angle is controllable by controlling the slope and length of the gliding surface as well as the distance that the electrode of the gliding catheter extends through the side-port opening. FIG. 6 is a fragmentary, isometric view of the diagnostic or treatment device 10 of FIGS. 1-5 with the gliding catheter 14 in the deployed configuration that is also depicted in FIG. 5.

Figure 7:
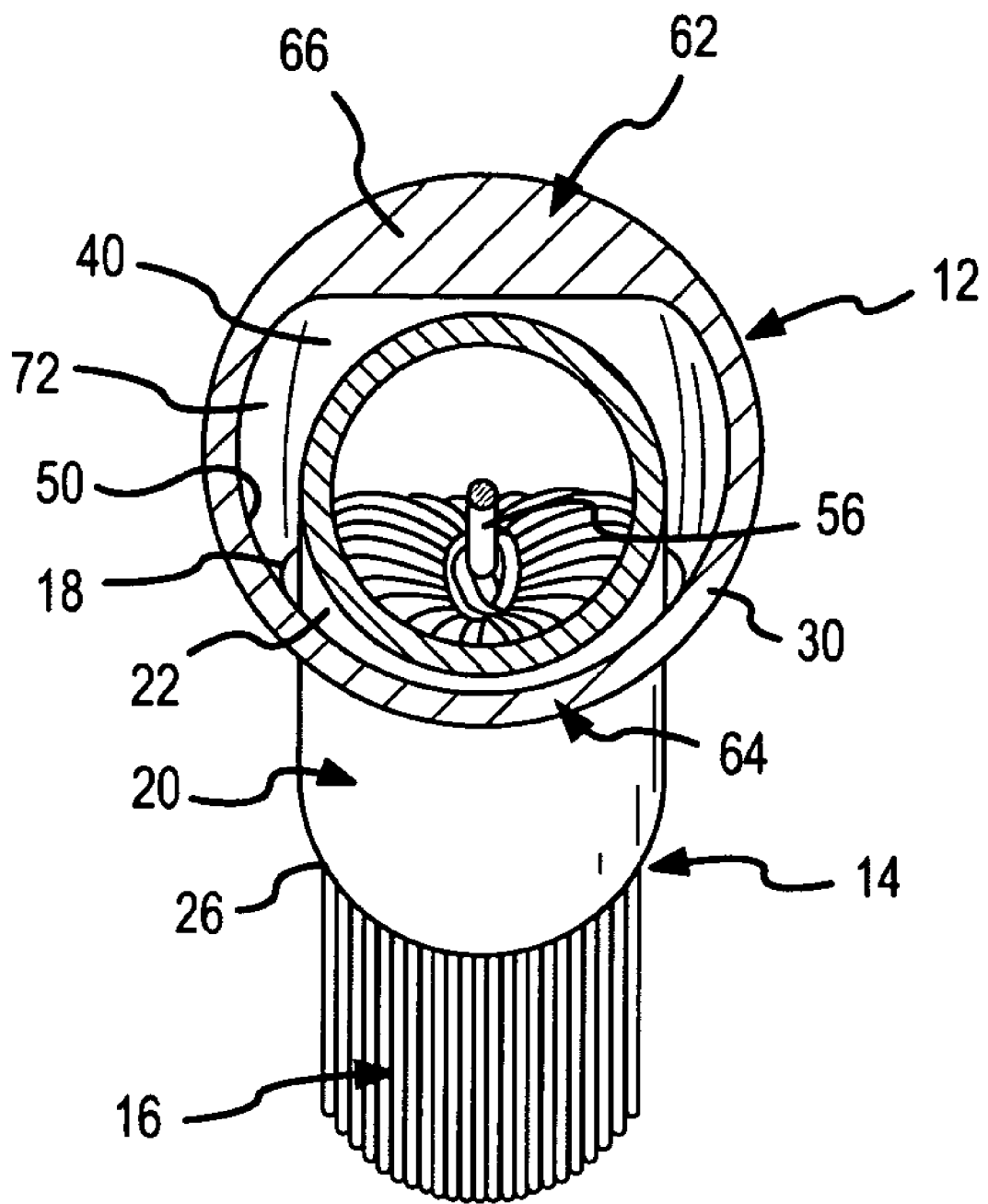
FIG. 7 is a cross-sectional view taken along line 7-7 of FIG. 5.

FIG. 7 is a cross-sectional view taken along line 7-7 of FIG. 5. As clearly shown in this figure, the upper wall 62 may include a thickened portion 66. When the brush electrode 16 is advanced into contact with tissue to be diagnosed or treated (see, e.g., FIGS. 8 and 9), the thickened portion 66 of the upper wall 62 may help prevent the side-port sheath 12 from flexing upward in the direction of arrow 68 (FIG. 8) as the electrode 16 impacts the tissue 70 (FIG. 8). As also clearly shown in FIG. 7, the catheter sheath 20 may fit loosely within the side-port sheath 12 to reduce the amount of friction that must be overcome to move the gliding catheter 14 relative to the side-port sheath 12 during placement and translation of the gliding catheter electrode. In other words, the outer surface 22 of the catheter sheath 20 may not be fully engaged by the inner surface 50 of the shaft 30 of the side-port sheath 12. As shown in this figure, the inner surface 50 of the shaft 30 of the side-port sheath 12 blends into a transition surface 72 that blends into the gliding surface 40. The inner surface 50, the transition surface 72, and the gliding surface 40 together guide the electrode 16 of the gliding catheter 14 toward the side-port opening 18. FIG. 7 also shows another view of the uninsulated portion 56 of the conductor 52 making contact with the bundle of filaments comprising the brush electrode 16 that is shown in the drawings as a sample gliding catheter.

FIGS. 8 and 9 are similar to FIG. 5, but show different configurations for the gliding surface. In particular, in FIG. 8, the tip 32' comprises a steep gliding surface 40', which forces the electrode 16 of the gliding catheter 14 to approach the tissue 70 to be treated or diagnosed at a steeper incidence angle 74 (i.e., closer to 90 degrees to the longitudinal axis of the device) between a longitudinal axis 76 of the side-port sheath 12 and a longitudinal axis 78 of the brush electrode 16 than is shown with the embodiment of FIGS. 4 and 5, for example. In contrast, in FIG. 9 the tip 32" comprises a shallow gliding surface 40'" resulting in shallow deployment of the electrode 16 of the gliding catheter toward the tissue 70. In FIG. 8, the working surface 28 at the distal end of the gliding catheter 14 is being directed toward the tissue 70, whereas, in FIG. 9, the side of the electrode 16 and the corner of the working surface 28 is making initial contact with the tissue 70 to be diagnosed or treated. The separation distance 80 between the diagnostic or treatment device and the tissue also influences what constitutes a desirable configuration (e.g., slope) for the gliding surface.

Figure 10:
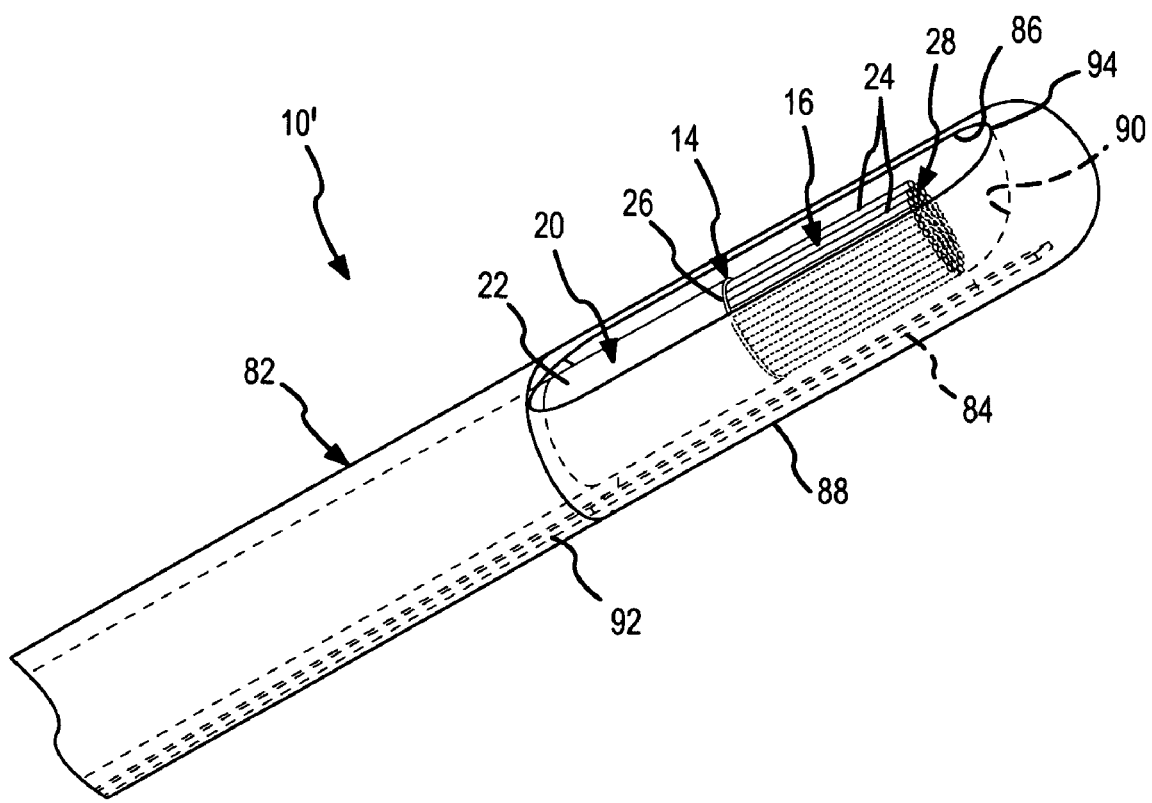
FIG. 10 is a fragmentary, isometric view of a diagnostic or treatment device comprising a side-port sheath according to a second embodiment of the present invention, and depicts a suspension ribbon in phantom alongside an undeployed gliding catheter adjacent to an elongated side-port opening.

FIG. 10 is a fragmentary, isometric view of a diagnostic or treatment device 10' comprising a side-port sheath 82 according to a second embodiment of the present invention. This figure is similar to FIG. 1, but depicts a deflection and suspension ribbon, wire, or strip 84 in phantom alongside an undeployed gliding catheter 14 that is adjacent to the elongated side-port opening 86 in the tip 88 of the side-port sheath 82. The suspension ribbon 84 may comprise, for example, a ribbon of Nitinol or NiTi. As shown to good advantage in FIG. 10, the curved surface 90 that extends from the upper wall 92 of the side-port sheath 82 to a distal edge 94 of the side-port opening 86 is steeper than the gliding surface 40 depicted in, for example, FIGS. 1-3. As explained further below, in this embodiment, the suspension ribbon 84 not only directs the gliding electrode catheter 14 toward the side-port opening 86, but also suspends the electrode 16. Since the suspension ribbon helps push the gliding electrode catheter 14 toward the side-port opening 86, the internal, curved surface 90 at the distal end of the tip 88 could be flat. If a flat surface replaced the curved surface 90 depicted in FIG. 10, the suspension ribbon would be solely responsible for directing the gliding electrode catheter 14 toward the side-port opening 86.

Figure 11:
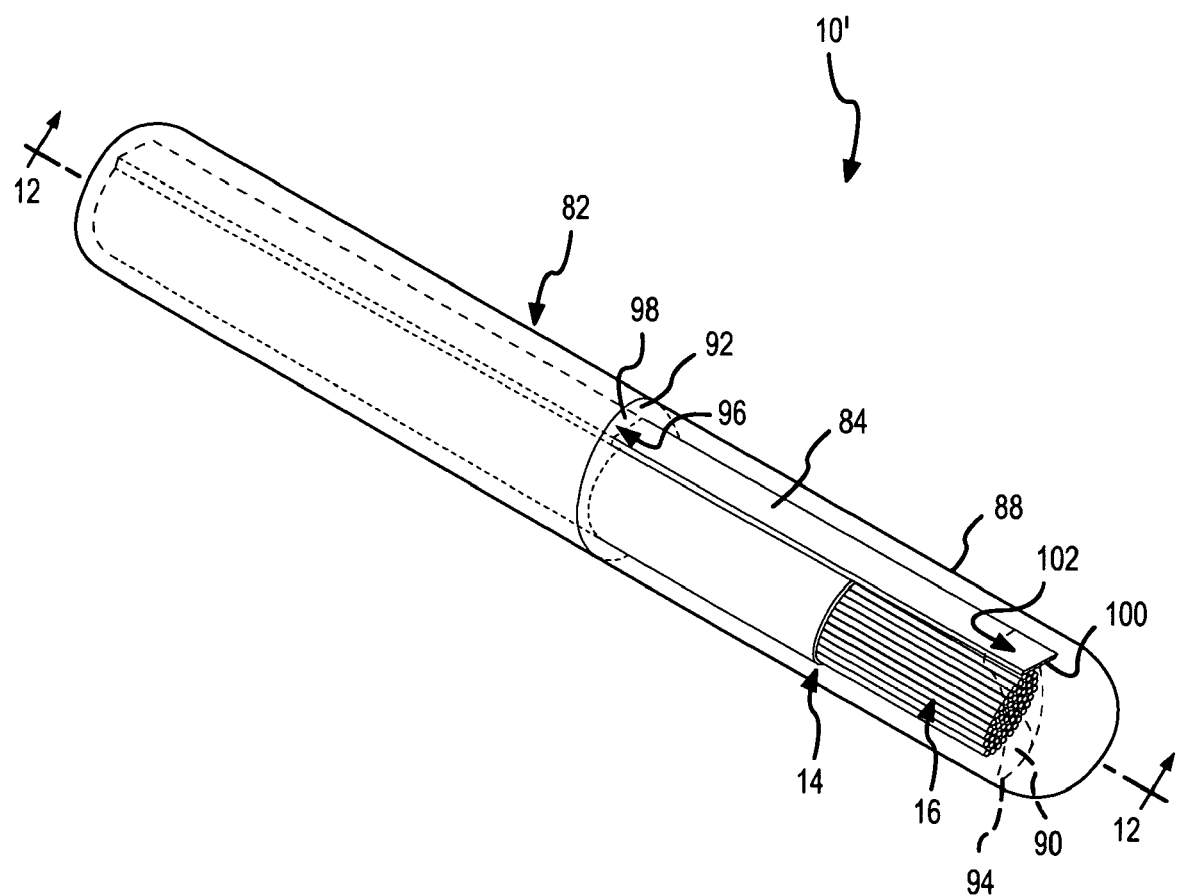
FIG. 11 is a fragmentary, isometric view of the diagnostic or treatment device depicted in FIG. 10 from a different angle, with a tip of the side-port sheath shown as partially transparent to reveal a portion of the suspension ribbon and a portion of the gliding catheter.

FIG. 11 is a fragmentary, isometric view of the diagnostic or treatment device 10' depicted in FIG. 10 from a different angle. In this figure, the tip 88 of the side-port sheath 82 is shown as partially "transparent" to reveal a portion of the suspension ribbon 84 and a portion of the gliding catheter 14. As shown in this figure and, for example, FIGS. 14 and 16, the suspension ribbon 84 is slideably mounted in a ribbon channel or slot 96 extending longitudinally through the thickened portion 98 of the shaft of the side-port sheath 82. As mentioned above in connection with the first embodiment 12 of the side-port sheath, the gliding catheter could be other than the brush-electrode catheter 14 depicted in the figures.

Figure 12:
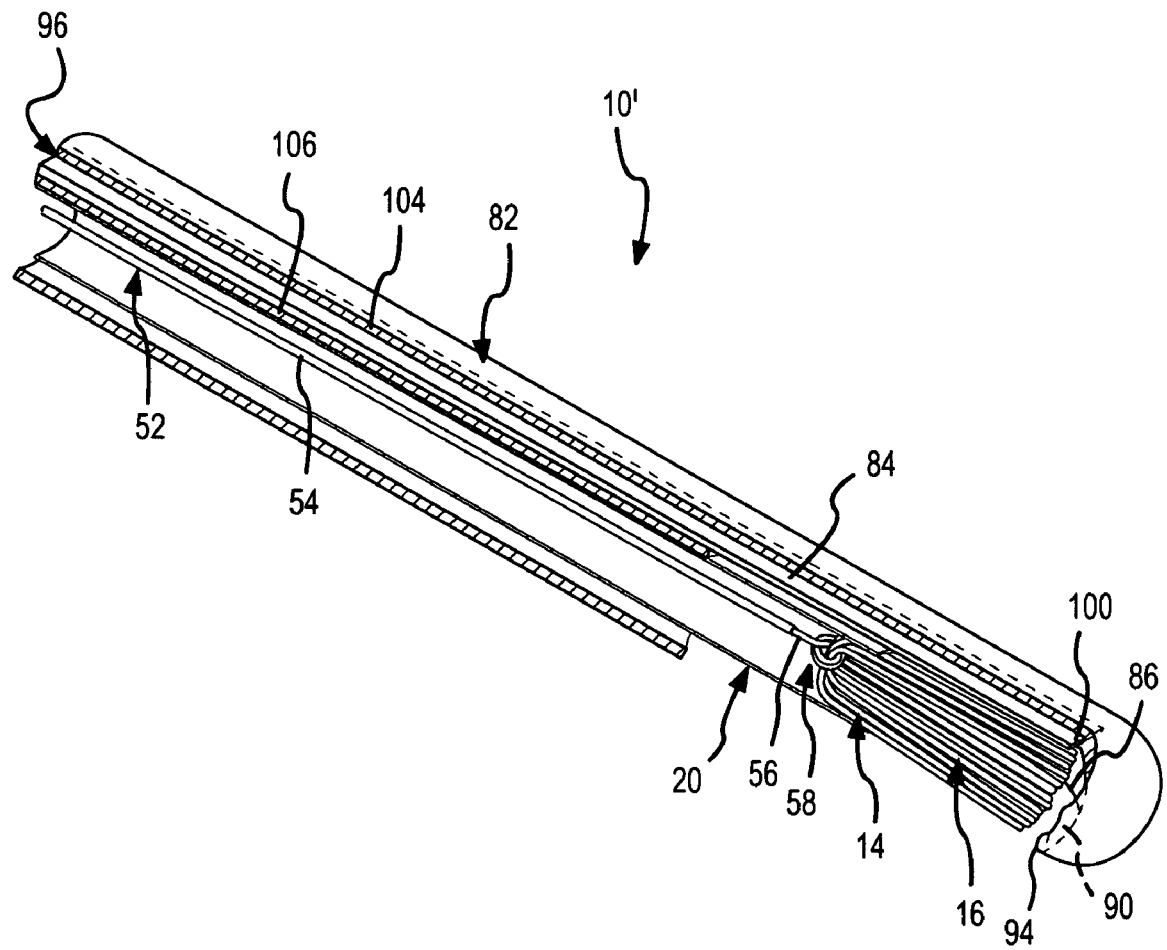
FIG. 12 is a fragmentary, isometric, cross-sectional view of the diagnostic or treatment device depicted in FIGS. 10 and 11 taken along line 12-12 of FIG. 11, with the gliding catheter depicted next to a curved surface leading to a distal edge of the elongated side-port opening.

FIG. 12 is a fragmentary, isometric, cross-sectional view of the diagnostic or treatment device 10' depicted in FIGS. 10 and 11 taken along line 12-12 of FIG. 11. In FIG. 12, however, the shaft and tip of the side-port sheath are depicted as a single, unitary component. This is an alternative construction to the two-piece construction depicted in, for example, FIGS. 10 and 11. The electrode 16 of the gliding catheter 14 is depicted in FIG. 12 next to the curved surface 90 that leads to the distal edge 94 of the elongated, side-port opening 86. Since the gliding catheter 14 is depicted in this figure as a brush electrode catheter, the conductor 52 is visible in this cross-sectional view, including the insulated portion 54 and the uninsulated portion 56 of the conductor. Again, the uninsulated portion of the conductor is shown as being looped around the bundle of filaments comprising the brush electrode 16 to transfer ablative energy to the brush electrode. The suspension ribbon 84 is depicted in place in the ribbon channel 96, and the distal end 100 of the suspension ribbon 84 is being supported by a short, ribbon containment cavity or slot 102 (see also FIG. 11). The ribbon channel 96 comprises an upper channel wall 104 and a lower channel wall 106, with the suspension ribbon 84 slideably positioned between the upper channel wall 104 and the lower channel wall 106.

Figure 13:
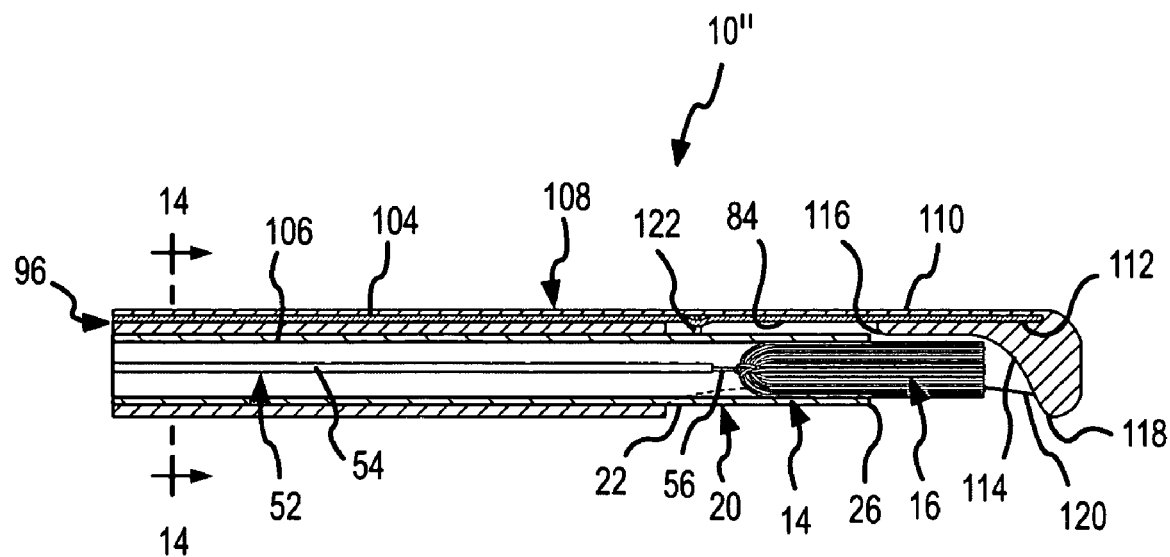
FIG. 13 is a fragmentary, cross-sectional view of a diagnostic or treatment device comprising a side-port sheath according to a third embodiment of the present invention, having a tip configuration that is different from the tip configuration of FIGS. 10-12.

FIG. 13 is a fragmentary, cross-sectional view of the diagnostic or treatment device 10" comprising a side-port sheath 108 according to a third embodiment of the present invention. This third embodiment of the present invention is similar to the second embodiment 82 depicted in FIGS. 10-12. In this third embodiment, however, the tip 110 of the side-port sheath 108 has a slightly different configuration from what is shown in FIGS. 10-12. In particular, the ribbon containment cavity or slot 112 depicted in FIG. 13 is elongated, and the internal, curved surface 114 is also elongated compared to the curved surface depicted in FIGS. 10-12. Thus, in this embodiment, a longer section of the distal portion of the suspension ribbon 84 is supported by the ribbon containment slot 112 formed in the tip 110 of the side-port sheath 108. Similar to what was shown in FIGS. 1-3, for example, the curved surface 114 depicted in FIG. 13 also comprises a proximal or leading edge 116 and a distal or trailing edge 118. The curved surface 114 depicted in FIG. 13, however, may better facilitate transition of the gliding catheter electrode 116 through the side-port opening 120. In particular, the leading edge 116 of the curved surface 114 is better configured in this embodiment to guide the distal edge 26 of the catheter sheath 20 toward the side-port opening 120. Finally, the embodiment depicted in FIG. 13 also differs from the embodiment depicted in FIGS. 10-12 in that it includes a ribbon guide 122 (see also FIG. 17) that slippingly links the suspension ribbon 84 to the sheath 20 of the gliding catheter 14, which provides advantages discussed further below.

Figure 14:
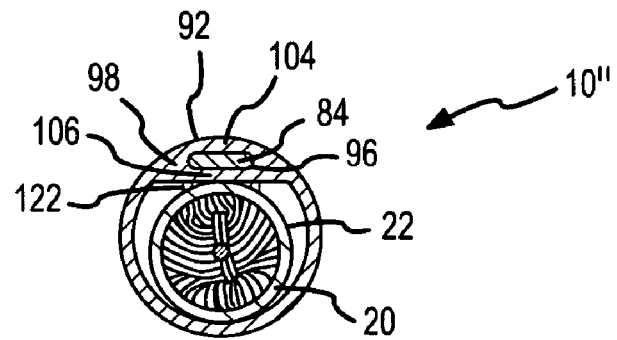
FIG. 14 is a cross-sectional view taken along line 14-14 of FIG. 13.

FIG. 14 is a cross-sectional view taken along line 14-14 of FIG. 13. As shown in this figure, the suspension ribbon 84 extends longitudinally through a thickened portion 98 of the shaft of the side-port sheath. In particular, the suspension ribbon 84 extends within the ribbon channel or slot 96 formed between the upper channel wall 104 and the lower channel wall 106. The ribbon guide 122, which extends around and contains the suspension ribbon 84, is also partially visible in FIG. 14.

Figure 15:
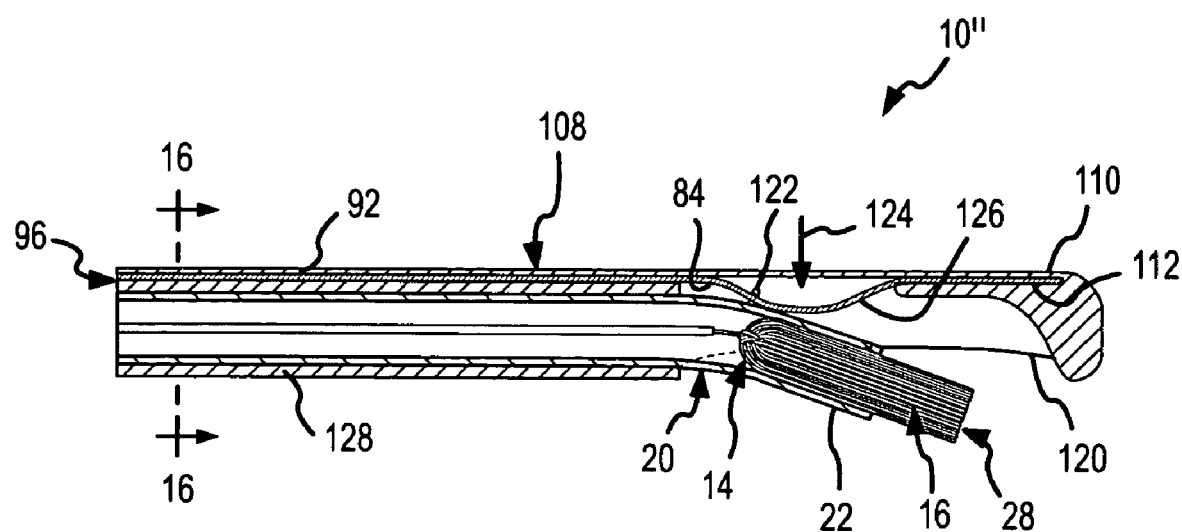
FIG. 15 is similar to FIG. 13, but depicts the gliding catheter in a deployed configuration after being guided partially through the side-port opening by a section of the suspension ribbon that acts like a leaf spring.

FIG. 15 is similar to FIG. 13, but depicts the gliding catheter 14 in a deployed configuration. In particular, in FIG. 15, the suspension ribbon 84 has been forced longitudinally toward the distal end of the side-port sheath 108. When the suspension ribbon is forced longitudinally toward the distal end of the side-port sheath, a portion of the suspension ribbon between the ribbon channel 96 and the ribbon containment cavity 112 bows in the direction of arrow 124 toward the side-port opening 120 (i.e., the only direction in which it can easily bow). The bowed portion of suspension ribbon forms a bowed leaf spring 126 that not only directs the gliding catheter electrode 16 through the side-port opening 120, but also suspends the gliding catheter electrode 16 against the tissue (see, e.g., FIGS. 18-20) being diagnosed or treated. The bowed leaf spring 126 thus helps to ensure that adequate contact is maintained between the electrode and the tissue. The ribbon guide 122, which is shown in cross-section in FIG. 15, helps prevent the suspension ribbon 84 from merely extending around and past the working surface 28 at the distal end of the gliding catheter 14 without pressing the gliding catheter through the side-port opening 120.

Figure 16:
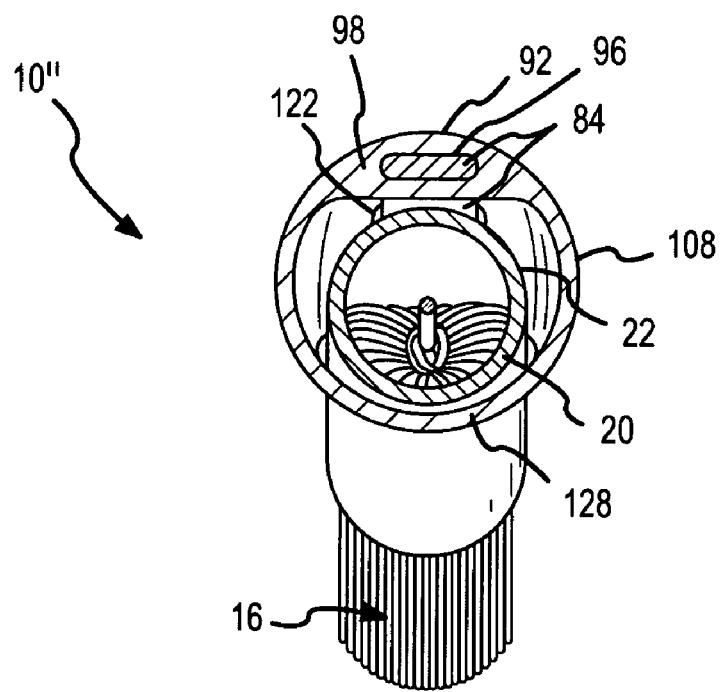
FIG. 16 is a cross-sectional view taken along line 16-16 of FIG. 15.

FIG. 16 is similar to FIG. 14, but is a cross-sectional view taken along line 16-16 of FIG. 15. Thus, the gliding catheter electrode 16, which is depicted in the figures as a brush electrode, is shown extending below the lower wall 128 of the shaft of the side-port sheath 108. The ribbon guide 122 may be seen in FIG. 16 extending around the suspension ribbon 84.

Figure 17:
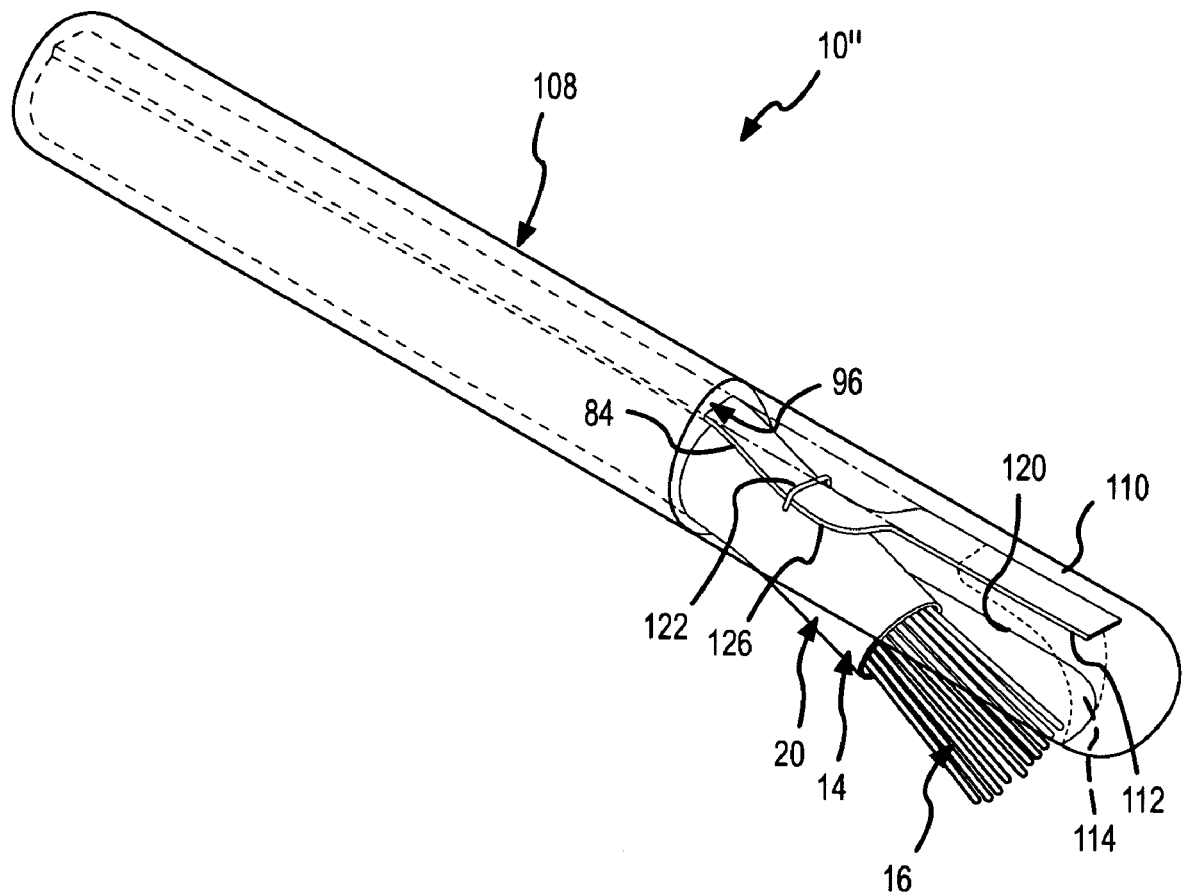
FIG. 17 is a fragmentary, isometric view of the diagnostic or treatment device of FIGS. 13-16 with the gliding catheter in the deployed configuration that is also depicted in FIGS. 15 and 16.

FIG. 17 is a fragmentary, isometric view of the diagnostic or treatment device 10" of FIGS. 13-16 with the gliding catheter 14 in the deployed configuration that is also depicted in FIGS. 15 and 16. In FIG. 17, a portion of the tip 110 of the side-port sheath 108 is shown as "transparent" to make it easy to comprehend how the bowed leaf spring 126 extends under the ribbon guide 122 and into contact with the sheath 20 of the gliding catheter 14. The suspension ribbon 84 is shown in the figures with a rectangular lateral cross section (i.e., the cross section taken perpendicular to the ribbon's longitudinal axis), which helps stabilize the suspension ribbon as it performs the pressing and suspending functions described above. The suspension ribbon may, however, have other than a rectangular cross section. And, as previously discussed, the side-port sheath is shown in most of the figures as comprising a separate shaft and tip joined at a seam, but the shaft and tip of the side-port sheath may comprise a unitary piece as shown in FIG. 12.

Figure 18:
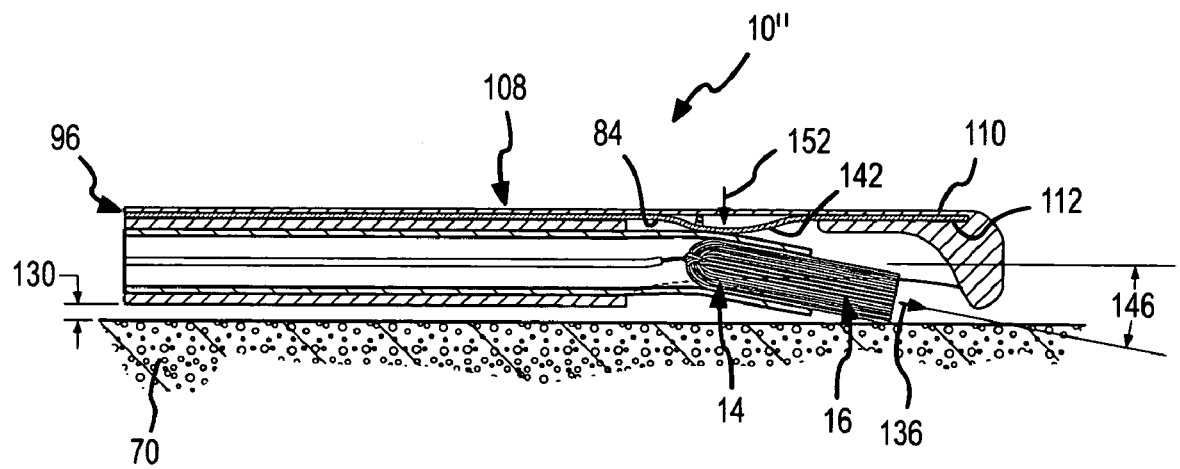
FIGS. 18-20 are similar to FIG. 15, but depict the gliding catheter being deployed toward tissue at various incidence angles depending upon the distance between the tissue and the diagnostic or treatment device.
Figure 19:
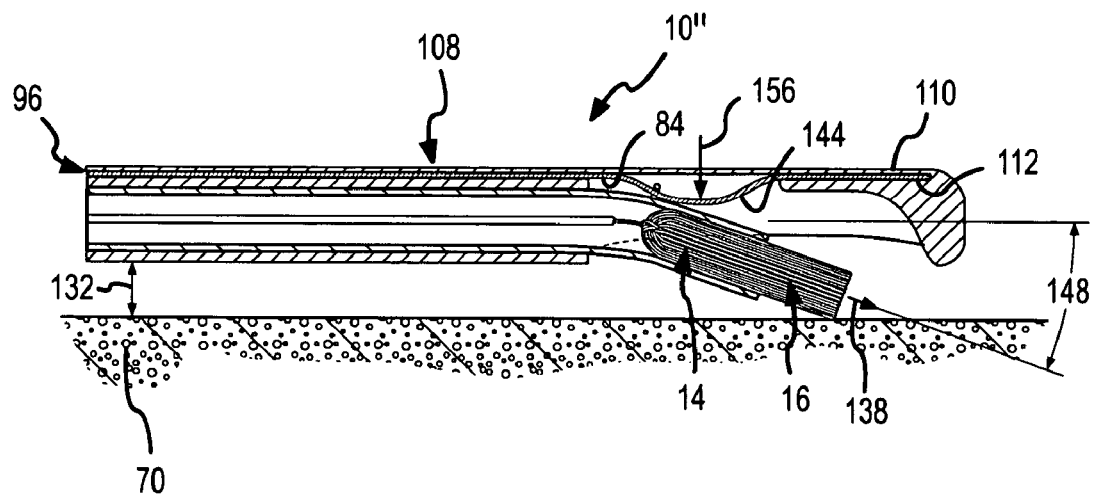
Figure 20:
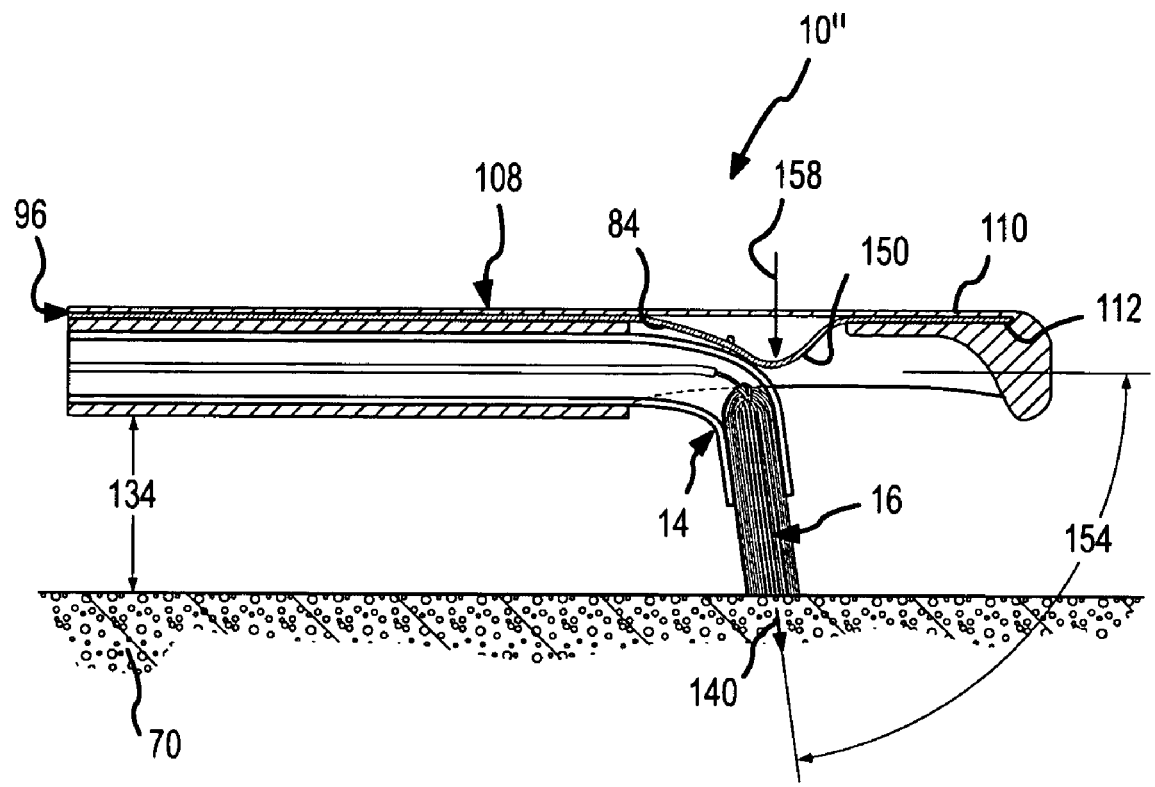

FIGS. 18-20 are similar to FIG. 15, but depict the gliding catheter 14 being deployed toward tissue 70 at various incidence angles depending upon the distance between the tissue and the diagnostic or treatment device 10' and the size of the bowed leaf spring. In FIG. 18, the separation distance 130 between the side-port sheath 108 and the tissue 70 to be diagnosed or treated is short. FIG. 19 depicts a separation distance 132 between the side-port sheath 108 and the tissue 70 to be diagnosed or treated that is greater than the separation distance 130 shown in FIG. 18. In FIG. 20, the separation distance 134 between the side-port sheath 108 and the tissue 70 to be diagnosed or treated is even greater than the separation distance 130 depicted in FIG. 18 and the separation distance 132 depicted in FIG. 19.

As the gliding catheter 14 is advanced in the direction of arrows 136 (FIG. 18), 138 (FIG. 19), or 140 (FIG. 20), the suspension ribbon 84 is also advanced toward the ribbon containment cavity 112 formed in the distal portion of the tip 110. The gliding catheter 14 and the suspension ribbon 84 may be advanced together, or they may be advanced separately. As more suspension ribbon 84 is forced toward the distal end of the diagnostic or treatment device 10", the size of the bowed leaf spring increases (compare, for example, the bowed leaf spring 142 of FIG. 18 to the bowed leaf spring 144 of FIG. 19), and the incidence angle at which the gliding catheter electrode is urged towards the tissue 70 to be treated or diagnosed becomes relatively steeper (compare, for example, the incidence angle 146 of FIG. 18 to the incidence angle 148 of FIG. 19).

In particular, in FIG. 18, a short section of the suspension ribbon forms the relatively-small, bowed leaf spring 142 (when compared to the bowed leaf springs 144, 150 depicted in FIGS. 19 and 20, respectively), which projects downwardly in the direction of arrow 152 away from the gap between the suspension ribbon channel 96 and the suspension ribbon containment cavity 112. The bowed leaf spring 142 thereby pushes the gliding catheter electrode 16 towards the tissue 70 at a relatively shallow incidence angle 146 when compared to the incidence angles 148, 154 depicted in FIGS. 19 and 20, respectively. In FIG. 19, a medium-length section of the suspension ribbon 84 projects downwardly in the direction of arrow 156 away from the gap between the suspension ribbon channel 96 and the suspension ribbon containment cavity 112. This medium-length section of the suspension ribbon 84 forms a medium-sized, bowed leaf spring 144 (when compared to the bowed leaf springs 142, 150 depicted in FIGS. 18 and 20, respectively), which pushes the gliding catheter electrode 16 towards the tissue 70 at a slightly steeper incidence angle 148 than what is shown in FIG. 18. In FIG. 20, a relatively-long section of the suspension ribbon 84 projects downwardly in the direction arrow 158 and forms the relatively-large, bowed leaf spring 150 (when compared to the bowed leaf springs 142, 144 depicted in FIGS. 18 and 19, respectively), which pushes the gliding catheter electrode 16 towards the tissue 70 at a relatively steep incidence angle 154 (i.e., approaching 90 degrees).

The suspension ribbon may, alternatively, be pinned or attached to the catheter sheath 20 of the gliding catheter 14. For example, in the second embodiment of the side-port sheath 82, which is depicted in FIGS. 10-12, the suspension ribbon may be attached to the outer surface 22 of the catheter sheath 20 a short distance proximal of the distal edge 26 of the catheter sheath. Similarly, in the third embodiment of the side-port sheath, which is depicted in FIGS. 13-20, the ribbon guide 122 may be used to attach the suspension ribbon 84 to the outer surface 22 of the catheter sheath 20. Thus, the suspension ribbon 84 may freely slide between the outer surface 22 of the catheter sheath 20 and the ribbon guide 122, or the suspension ribbon may be pinned or tacked to the outer surface 22 of the catheter sheath 20 by the ribbon guide 122. Also, the suspension ribbon 84 may be directly connected to the outer surface 22 of the catheter sheath 20.

Figure 21:
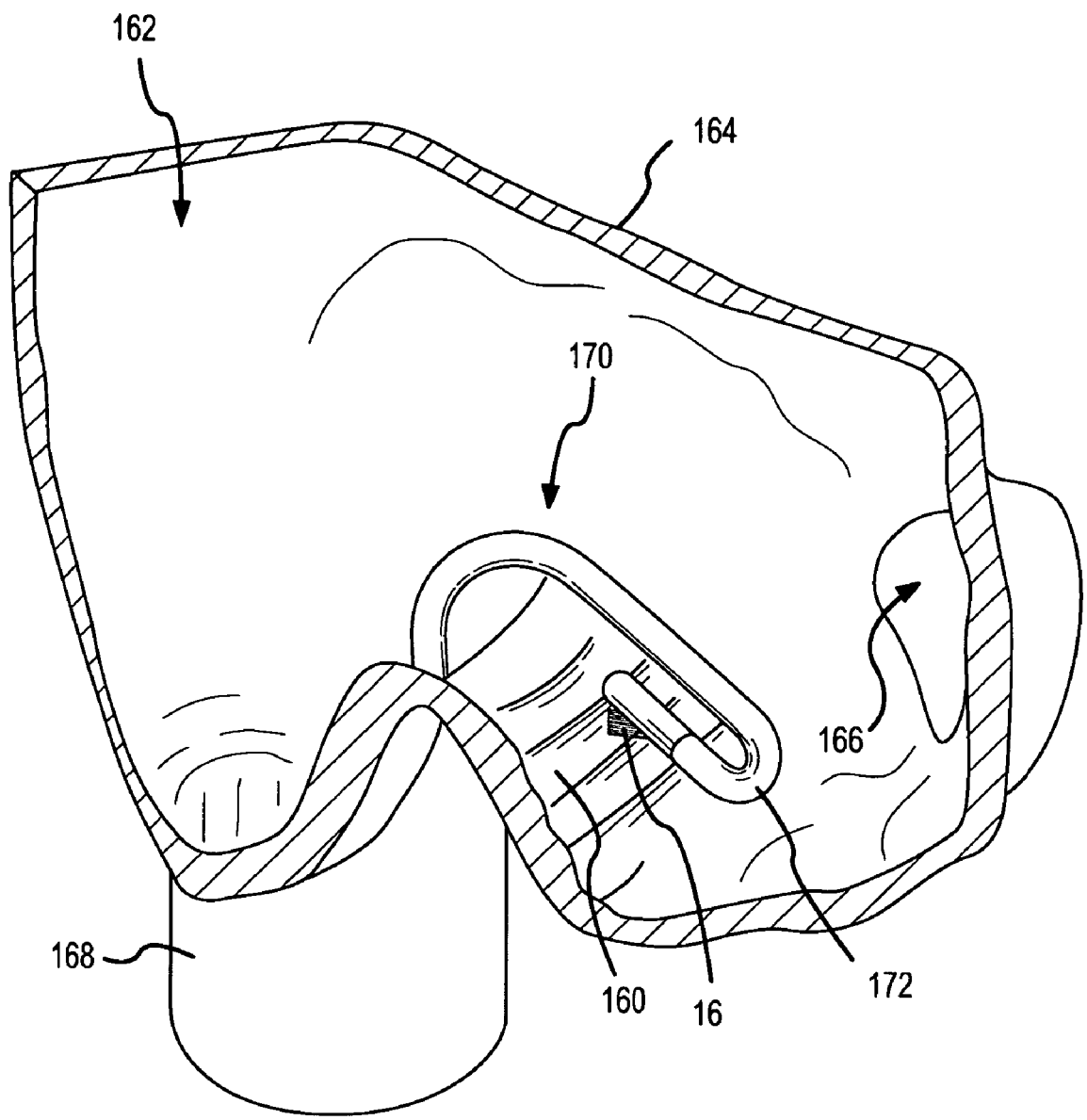
FIGS. 21-23 are schematic, fragmentary, isometric views of diagnostic or treatment devices comprising the side-port sheaths according to the present invention being used to form lesions in the right atrium of a heart.
Figure 22:
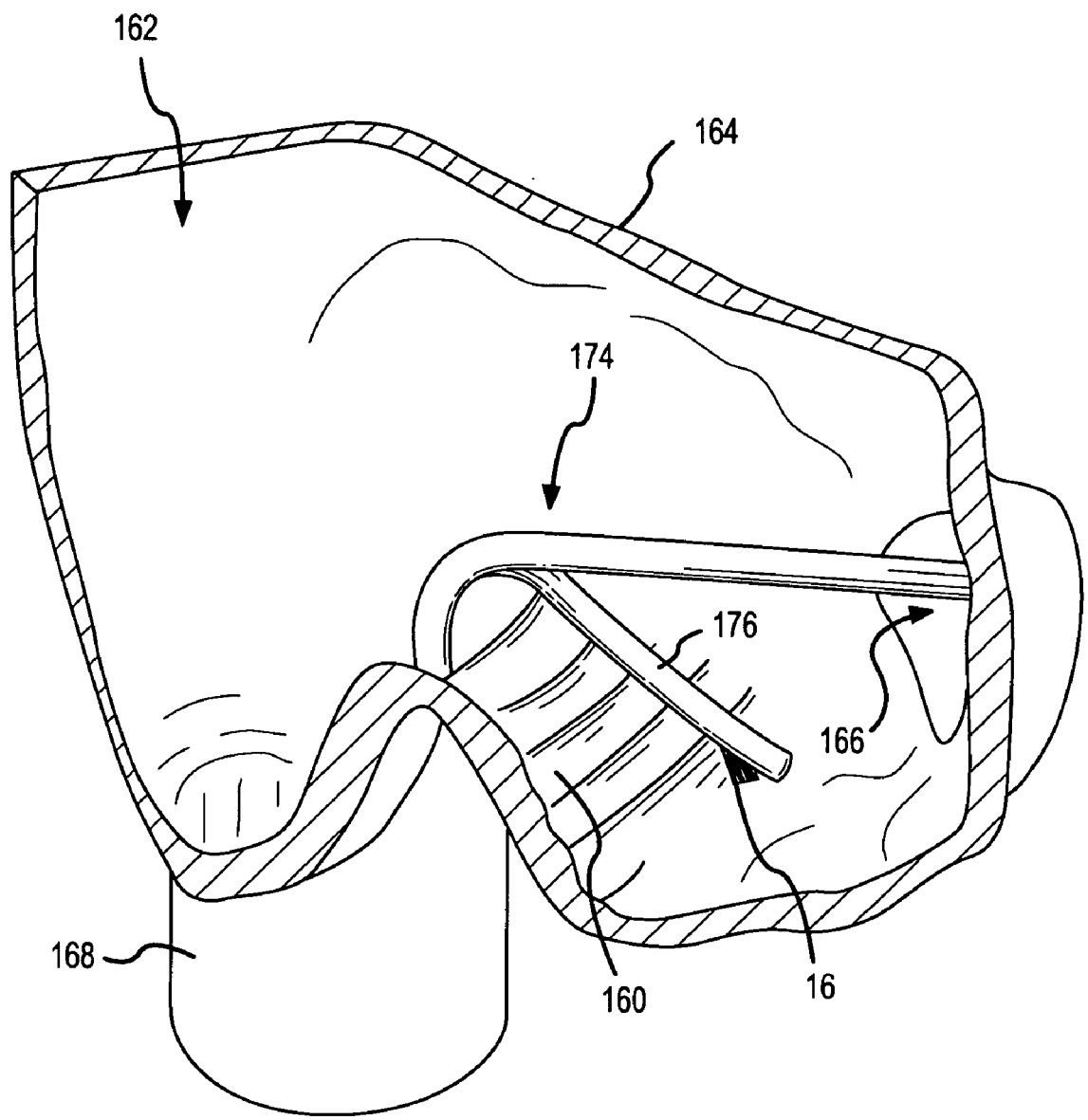
Figure 23:
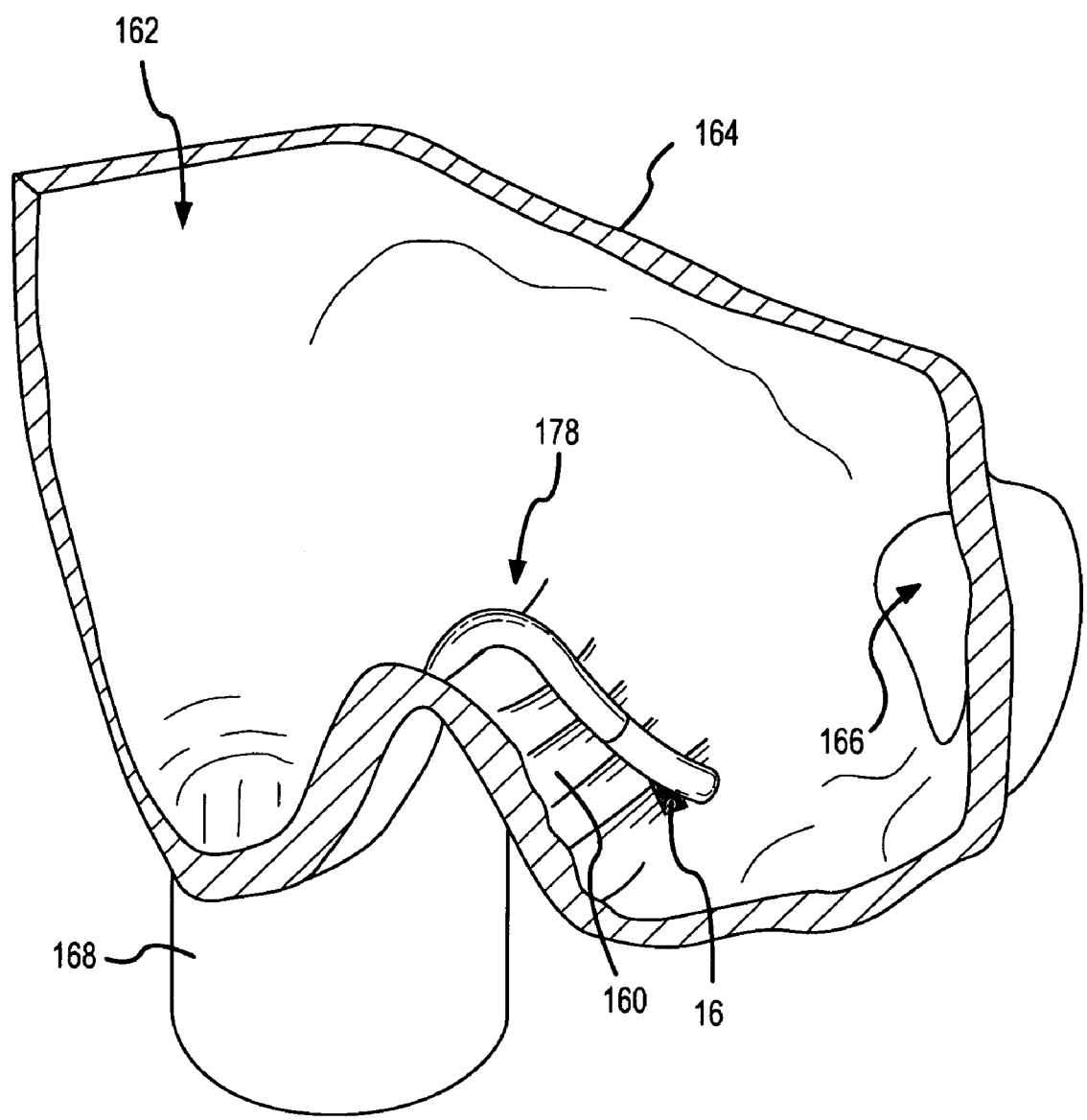

FIGS. 21-23 are schematic, fragmentary, isometric views of diagnostic or treatment devices comprising side-port sheaths according to the present invention being used to form lesions on a trabeculated surface 160 in the right atrium 162 of a heart 164. In particular, these figures depict a portion of the right atrium 162 with part of the heart wall broken away to reveal a trabeculated surface 160 (e.g., the isthmus between the tricuspid valye 166 and the inferior vena cava 168) being diagnosed or treated. The side-port sheaths depicted in FIGS. 21-23 have various pre-formed shapes and curvatures to position the side-port opening facing the tissue to be diagnosed or treated so that the gliding catheter is in close proximity to, or in contact with, the tissue to be diagnosed or treated.

The diagnostic or treatment device 170 depicted in FIG. 21 is a "single-anchored configuration," where the side-port sheath 172 rests directly on, and is supported, or stabilized by, the trabeculated surface 160 itself. In FIG. 21, an electrode 16 of a deployed gliding catheter 14 (i.e., a brush electrode catheter) is shown in contact with the trabeculated surface 160. The side-port sheath 172 itself may be moved longitudinally while the gliding catheter 14 is deployed to create a spot or linear lesion on the trabeculated surface 160. Alternatively, or at the same time, the gliding catheter 14 may be moved relative to the side-port sheath 172 to achieve the desired lesion. Real-time monitoring of impedance, for example, may be used during a procedure to ensure that desired contact between the electrode 16 and the tissue is being maintained.

FIG. 22 is similar to FIG. 21, but depicts a diagnostic or treatment device 174 having a "dual-anchored configuration." In particular, the depicted device 174 rests against and is supported by the inferior vena cava 168, and a portion of the device is supported by the tricuspid valye 166 or the area around the tricuspid valye. Again, the side-port sheath 176 is thereby positioned in close proximity to, or in contact with, the trabeculated surface 160 to be diagnosed or treated in the manner described in the last paragraph.

FIG. 23 is similar to FIGS. 21 and 22, but depicts a diagnostic or treatment device 178 with an alternative, "single-anchored configuration." In this configuration, the device 178 includes a short cantilever section that is supported by the wall of the inferior vena cava 168. Once in place on the tissue to be diagnosed or treated, the device depicted in FIG. 23 is used in the same manner discussed in connection with description of FIG. 21.

Figure 24:
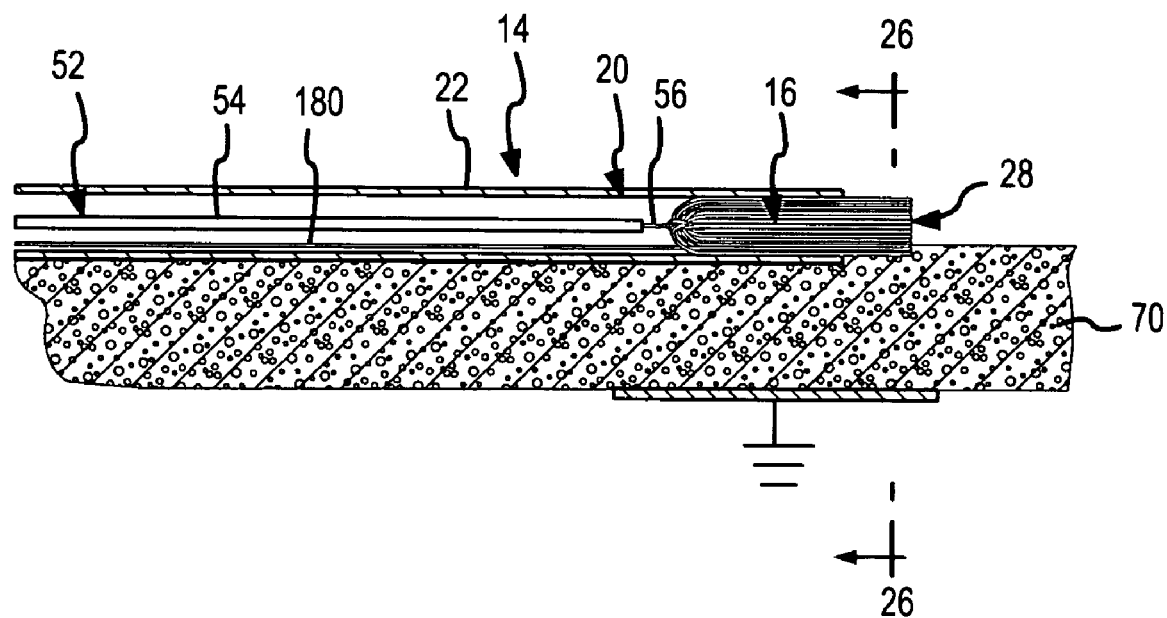
FIG. 24 depicts the gliding catheter shown in, for example, FIGS. 1 and 10 separated from the side-port sheath of the present invention and against tissue to be ablated.
Figure 25:
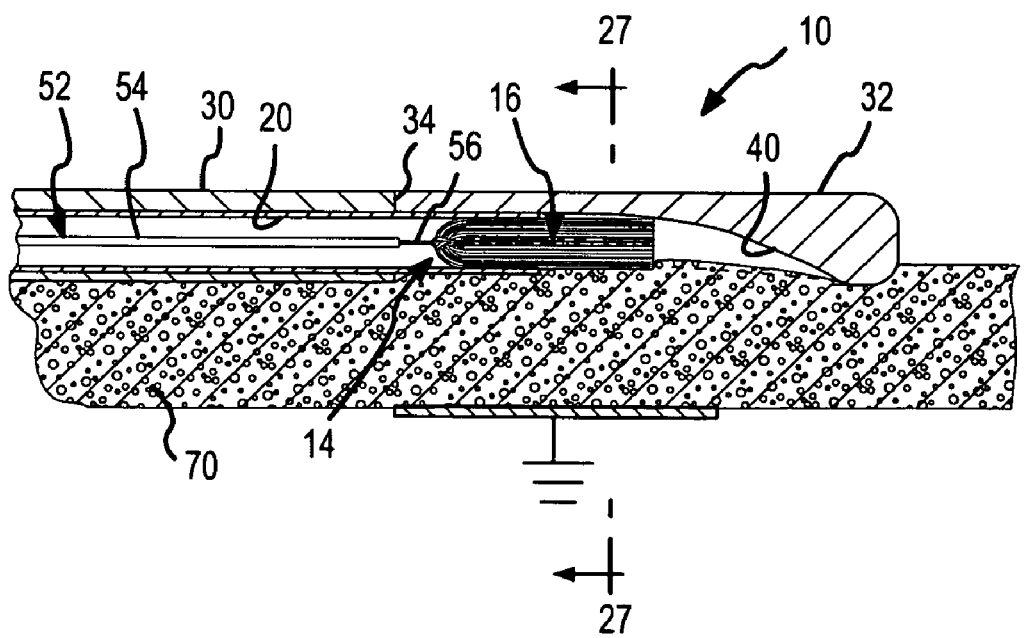
FIG. 25 depicts the diagnostic or treatment devices comprising the side-port sheath of FIGS. 1-7 against tissue to be ablated.
Figure 26:
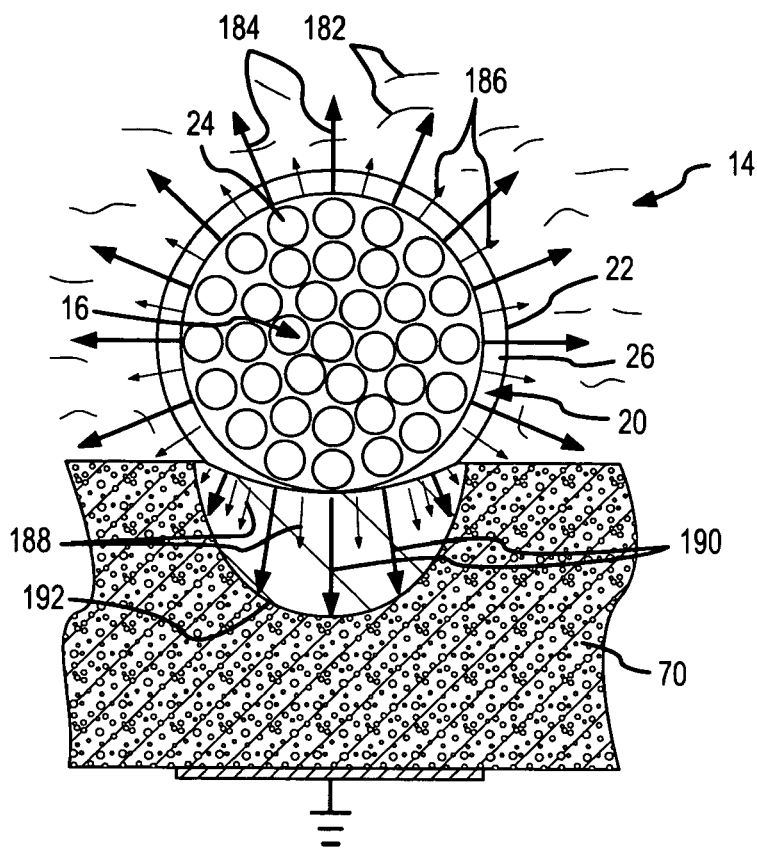
FIG. 26 is a schematic, cross-sectional view taken along line 26-26 of FIG. 24.
Figure 27:
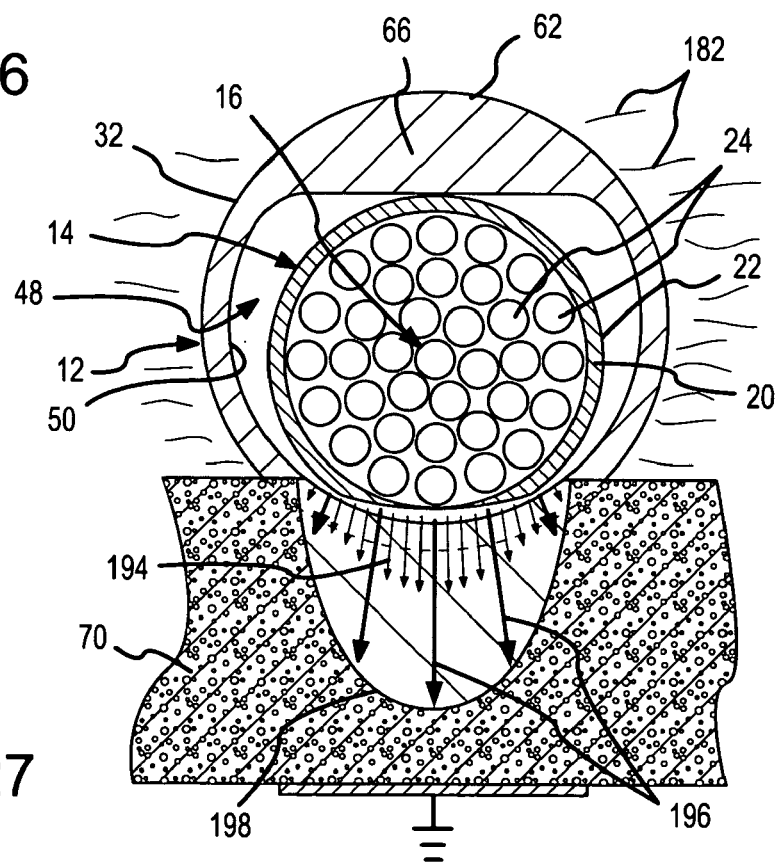
FIG. 27 is a schematic, cross-sectional view taken along line 27-27 of FIG. 25.

FIG. 24 depicts the gliding catheter 14 shown in, for example, FIGS. 1 and 10 separated from the side-port sheath of the present invention and lying against tissue 70 to be ablated. The gliding catheter 14 depicted in FIG. 24 also includes a secondary lead 180 in electrical or chemical communication with the brush electrode 16. It is apparent from FIG. 24 that the gliding catheter 14 (i.e., the brush electrode catheter in this figure) is being pressed toward the tissue 70 since a portion of the catheter sheath and the brush electrode is slightly embedded into the tissue 70. FIG. 26 is a schematic, cross-sectional view taken along line 26-26 of FIG. 24 and also clearly shows that the brush electrode catheter 14 is being pressed slightly into the tissue 70. FIG. 25 depicts the diagnostic or treatment device 10 comprising the side-port sheath of FIGS. 1-7 being pressed against tissue 70 that is being ablated. The gliding catheter 14 is in its undeployed configuration. FIG. 27 is a schematic, cross-sectional view taken along line 27-27 of FIG. 25 and clearly shows that the device is being slightly pressed into the tissue 70 that is being treated.

Comparing FIG. 26 to FIG. 27, it is apparent that the side-port sheath of the present invention provides some distinct advantages over an ablation catheter 14 without a side-port sheath. As shown in these figures, ambient fluid 182 (e.g., blood) surrounds the catheter electrode 16. In FIG. 26, ablative energy 184 from conductive filaments 24 comprising part of the brush electrode 16 is leaking to the ambient fluid 182 rather than being delivered to the tissue 70. Similarly, ablative energy 186 being carried in conductive fluid (e.g., saline) flowing between and among the filaments is also leaking to the ambient fluid 182. FIG. 26 also shows ablative energy 188 being delivered to the tissue by the conductive fluid, and ablative energy 190 being delivered to the tissue by the conductive filaments. The ablative energy 188, 190 being delivered to the tissue 70 is thus forming a lesion having the arcuate lesion boundary 192 depicted in FIG. 26.

In FIG. 27, on the other hand, the side-port sheath 12 inhibits or eliminates leakage of ablative energy to the ambient fluid 182. Thus, more ablative energy, whether ablative energy 194 delivered by the conductive fluid, if present, or ablative energy 196 delivered by the conductive filaments comprising part of the gliding catheter electrode 16, is delivered to the tissue 70, resulting in an arcuate lesion boundary 198 that extends deeper in to the tissue 70 than does the lesion boundary 192 depicted in FIG. 26 (assuming a relatively constant amount of total ablative energy is being delivered to the gliding catheter electrode 16 in FIGS. 26 and 27). The side-port sheath thereby enhances ablation efficiency. In tests, using a device similar to the device depicted in FIGS. 25 and 27, a wet-brush catheter was inserted in a side-port sheath and used to create a lesion. During the tests, 5-7 millimeter deep lesions were formed in 60 seconds at 10-20 watts of power and 6-12 milliliters per minute of saline flow through the brush electrode.

Figure 28:
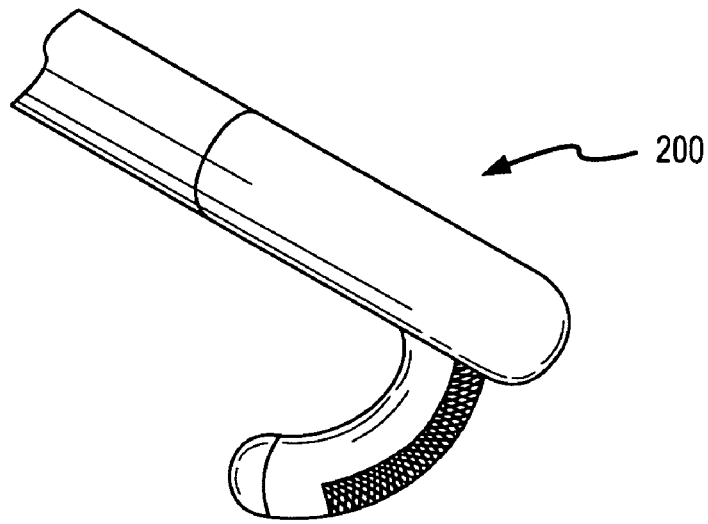
FIGS. 28-32 depict devices comprising the side-port sheaths according to the present invention being used with various different types of gliding catheters.
Figure 29:
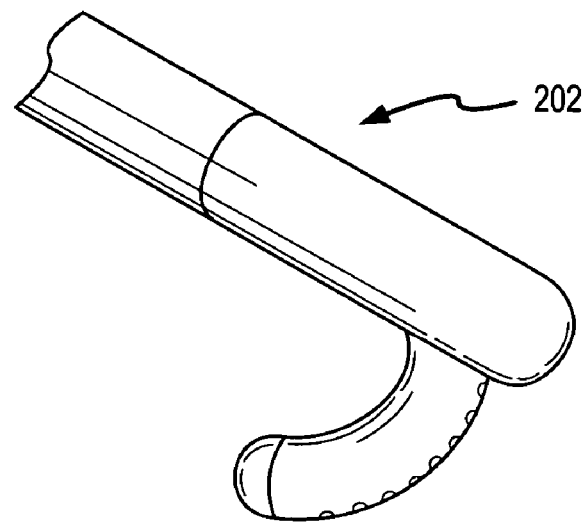
Figure 30:
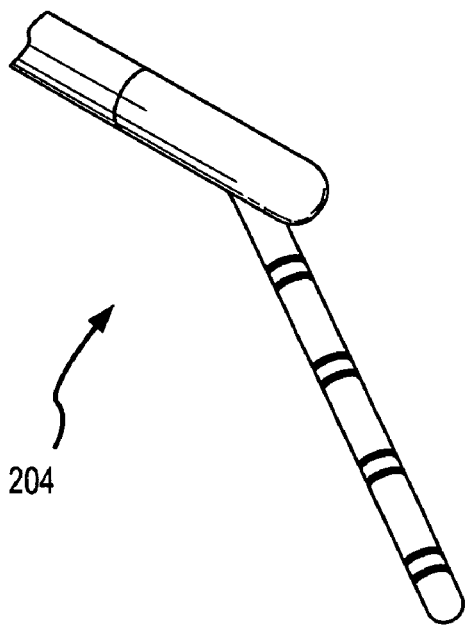
Figure 31:
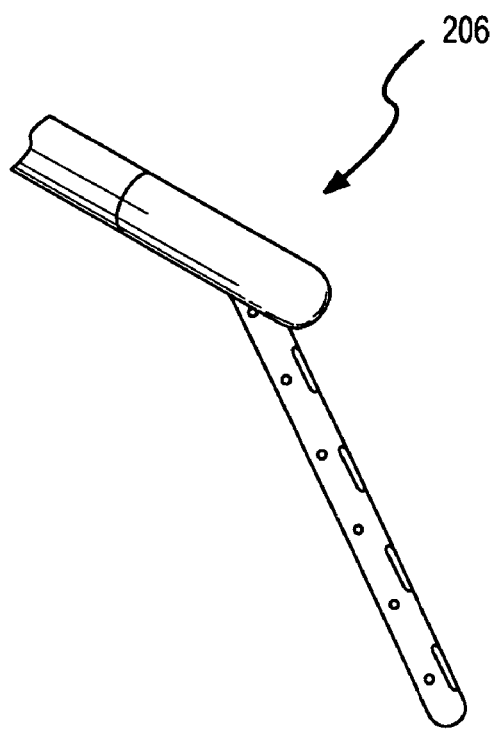
Figure 32:
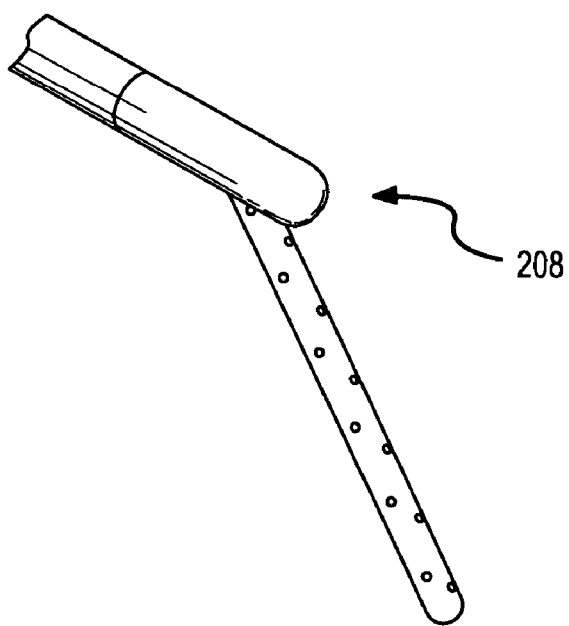

FIGS. 28-30 depict diagnostic or treatment devices (200, 202, 204, 206, 208) comprising the side-port sheaths according to the present invention being used with various different types of gliding catheters. These figures show that alternative catheter configurations may be used in combination with the side-port sheaths according to the present invention.

Although several embodiments of this invention have been described above with a certain degree of particularity, those skilled in the art could make numerous alternations to the disclosed embodiments without departing from the spirit or scope of this invention. All directional references are only used for identification purposes to aid the reader's understanding of the present invention, and do not create limitations, particularly as to the position, orientation, or use of the invention. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A device for the diagnosis or treatment of tissue in a body cavity, the device comprising
    a side-port sheath comprising a tip, wherein said tip further comprises
    a tip sidewall;
    an elongate tip side-port opening that extends through said tip sidewall from a proximal opening edge to a distal opening edge;
    an internal, gliding surface that extends from a leading edge to a trailing edge, wherein said trailing edge of said gliding surface is adjacent to said distal edge of said side-port opening; and
    an electrophysiology catheter comprising a catheter sheath and a catheter electrode; wherein
    said catheter sheath comprises a distal end, and
    said catheter electrode is a wet-brush electrode comprising a plurality of filaments extending from said distal end of said catheter sheath and wherein interstitial gaps are defined among said plurality of filaments and adapted to channel fluid through said plurality of filaments.

2. The device of claim 1, wherein said electrophysiology catheter comprises a catheter sheath having an outside surface, and wherein said elongate side-port sheath further comprises a shaft having an inner surface defining a longitudinally-extending lumen through which said catheter sheath slippingly extends.

3. The device of claim 2, wherein said shaft of said elongate side-port sheath is separate from said tip of said side-port sheath, and wherein said shaft and tip are joined at a seam.

4. The device of claim 2, wherein said shaft of said side-port sheath and said tip of said side-port sheath for a unitary piece.

5. The device of claim 1, wherein a taper is present at said proximal opening edge of said elongate tip side-port opening.

6. The device of claim 1, wherein said electrophysiology catheter is a gliding catheter.

7. The device of claim 6, wherein said catheter electrode is a flush-cooled electrode.

8. The device of claim 1 further comprising a conductor of ablative energy in electrical contact with said wet-brush electrode at a connection point.

9. The device of claim 1, wherein said tip is porous.

10. The device of claim 1, wherein said tip sidewall further comprises a tip upper wall and a tip lower wall, wherein said elongate tip side-port opening extends through said tip lower wall, and wherein said tip upper wall comprises a thickened portion.

11. The device of claim 10, wherein said side-port sheath further comprises a shaft having a shaft upper wall and a shaft lower wall, wherein said shaft upper wall comprises a thickened portion, wherein said shaft upper wall is aligned with said tip upper wall, wherein said shaft lower wall is aligned with said tip lower wall, and wherein said device further comprises a suspension ribbon slideably mounted in a ribbon channel extending within said thickened portion of said shaft upper wall.

12. A method of placing and translating a catheter in a body cavity having tissue to be diagnosed or treated, the method comprising the steps of
- assembling a side-port sheath comprising a tip, wherein said tip further comprises
  - a tip sidewall;
  - an elongate tip side-port opening that extends through said tip sidewall from a proximal edge to a distal edge; and
  - an internal, gliding surface that extends from a leading edge to a trailing edge, wherein said trailing edge of said gliding surface is adjacent to said distal edge of said elongate tip side-port opening;
- inserting an electrophysiology catheter having a working portion into said side-port sheath, with said working portion fully housed within said tip of said side-port sheath and adjacent to said elongate tip side-port opening;
- said working portion comprising a wet-brush electrode comprising a plurality of filaments extending from said distal end of said catheter sheath;
- positioning said side-port sheath into a body cavity with said elongate tip side-port opening adjacent to the tissue to be diagnosed or treated; and
- deploying said electrophysiology catheter by pushing said electrophysiology catheter toward said gliding surface of said side-port sheath until said working portion of said electrophysiology catheter at least partially exits said elongate tip side-port opening.

13. The method of claim 12 further comprising the step of adjusting the configuration of said gliding surface for a particular application.

14. The method of claim 12 further comprising the step of adjusting a separation distance between the tissue to be diagnosed or treated and said elongate tip side-port opening to adjust an angle at which said working portion of said electrophysiology catheter approaches the tissue.

15. The method of claim 12 further comprising the step of translating said electrophysiology catheter by alternately pushing said electrophysiology catheter out of said elongate tip side-port opening and pulling said electrophysiology catheter into said elongate tip side-port opening to make desired contact with the tissue.

16. The method of claim 15 further comprising the step of monitoring impedance during said translating step.

17. The method of claim 15, wherein said translating step further comprises translating said side-port sheath.

* * * * *